(12) United States Patent
Miyazaki et al.

(10) Patent No.: US 12,329,508 B2
(45) Date of Patent: Jun. 17, 2025

(54) MRI APPARATUS

(71) Applicants: CANON MEDICAL SYSTEMS CORPORATION, Otawara (JP); The Regents of the University of California, Oakland, CA (US)

(72) Inventors: Mitsue Miyazaki, Poway, CA (US); Won Bae, San Diego, CA (US); Vadim Malis, San Diego, CA (US); Yoshimori Kassai, Nasushiobara (JP)

(73) Assignees: CANON MEDICAL SYSTEMS CORPORATION, Otawara (JP); The Regents of the University of California, Oakland, CA (US)

( * ) Notice: Subject to any disclaimer, the term of this patent is extended or adjusted under 35 U.S.C. 154(b) by 144 days.

(21) Appl. No.: 18/166,061

(22) Filed: Feb. 8, 2023

(65) Prior Publication Data

US 2023/0248256 A1  Aug. 10, 2023

Related U.S. Application Data

(60) Provisional application No. 63/308,560, filed on Feb. 10, 2022.

(51) Int. Cl.
*A61B 5/055* (2006.01)
*A61B 5/00* (2006.01)

(52) U.S. Cl.
CPC ............ *A61B 5/055* (2013.01); *A61B 5/0042* (2013.01)

(58) Field of Classification Search
CPC ............................. A61B 5/0042; A61B 5/055
See application file for complete search history.

(56) References Cited

U.S. PATENT DOCUMENTS

| 9,545,206 | B2 | 1/2017 | Miyazaki et al. |
| 9,681,821 | B2 | 6/2017 | Piron et al. |
| 10,368,777 | B2 * | 8/2019 | Zhou ............ A61B 5/0044 |
| 10,799,141 | B1 * | 10/2020 | Damadian ........ A61B 5/704 |

(Continued)

OTHER PUBLICATIONS

Martina Absinta, et al., Human and nonhuman primate meninges harbor lymphatic vessels that can be visualized noninvasively by MRI, eLife, elifesciences.org. Short Report, 15 pgs.

(Continued)

*Primary Examiner* — Gregory H Curran
(74) *Attorney, Agent, or Firm* — Oblon, McClelland, Maier & Neustadt, L.L.P.

(57) ABSTRACT

In one embodiment, an MRI apparatus includes: a scanner that includes a static magnetic field magnet, a gradient coil, and a WB coil; and processing circuitry. The processing circuitry is configured to: cause the scanner to image, under a first imaging method, a tissue including a perfusion route of body fluid that removes waste products of the object the body fluid including neurofluid; generate an anatomical image of the tissue from first data acquired by imaging under the first imaging method; cause the scanner to image perfusion behavior of the body fluid in real time under a second imaging method using non-contrast perfusion imaging; generate a perfusion image indicating the perfusion behavior of the body fluid from second data acquired by imaging under the second imaging method; and generate a fused image by combining the anatomical image and the perfusion image.

20 Claims, 21 Drawing Sheets

(56) References Cited

U.S. PATENT DOCUMENTS

| | | |
|---|---|---|
| 10,905,354 B2 * | 2/2021 | Sakashita .............. G06T 5/50 |
| 10,912,470 B2 | 2/2021 | Tong et al. |
| 2013/0289387 A1 | 10/2013 | Shiodera et al. |
| 2015/0338489 A1 | 11/2015 | Nitta et al. |

OTHER PUBLICATIONS

Geir Ringstad, et al., Cerebrospinal fluid tracer offlux to parasagittal dura in humans, Nature Communications, Article, https://doi.org/10.1038/s41467-018-14185-x, 10 pgs.

William A. Copen, M.D., et al., MR Perfusion Imaging in Acute Ischemic Stroke, NIH Public Access, Author Manuscript. *Neuroimaging Clin N Am*. Author manuscript; available in PMC May 1, 2012, Published in final edited form as: Neuroimaging Clin N Am, May 2011: 21(2): 259-283. doi: 10.1016/j.nic.2011.02.007, 38 pgs.

Extended European Search Report issued on Jun. 22, 2023 in European Patent Application No. 23156119.2, 12 pages.

Li Zhao and David C. Alsop: "Characterizing Perfusion and Arterial Transit Time of the Choroid Plexus with Arterial Spin Labeling", Proceedings of the International Society for Magnetic Resonance in Medicine, ISMRM, Joint Annual Meeting ISMRM-ESMRMB, Paris, France, Jun. 16-21, 2018, No. 2028, Jun. 1, 2018 (Jun. 1, 2018), XP040701236, 4 pages.

Xingfeng Shao et al: "High resolution imaging of choroid plexus blood flow with multi-delay pseudo-continuous arterial spin labeling", Proceedings of The 2021 ISMRM & SMRT Annual Meeting & Exhibition, May 15-20, 2021, ISMRM, 2030 Addison Street, 7th Floor, Berkeley, CA 94704 USA, No. 2361, Apr. 30, 2021 (Apr. 30, 2021), XP040724380, 4 pages.

Joseph Charles R et al: "Pilot study utilizing MRI 3D TGSE PASL (arterial spin labeling) differentiating clearance rates of labeled protons in the CNS of patients with early Alzheimer disease from normal subjects", Magnetic Resonance Materials in Physics, Biology and Medicine, Springer, DE, GB, vol. 33, No. 4, Jan. 3, 2020 (Jan. 3, 2020), pp. 559-568, XP037188857, ISSN: 0968-5243, DOI: 10.1007/S10334-019-00818-3 [retrieved on Jan. 3, 2020].

Malis Vadim et al: "Age-related Decline of Intrinsic Cerebrospinal Fluid Outflow in Healthy Humans Detected with Non-contrast Spin-labeling MR Imaging", Magnetic Resonance in Medical Sciences, Dec. 17, 2022 (Dec. 17, 2022), XP93053536, JP ISSN: 1347-3182, DOI: 10.2463/mrms.mp.2022-0117. 14 pages.

\* cited by examiner

PERFUSION IMAGE

IM(perfusion)

TAG-ON IMAGE

IM(ON)

$$IM(perfusion) = \frac{||IM(OFF) - IM(ON)||}{|IM(OFF)|}$$

TAG-OFF IMAGE

IM(OFF)

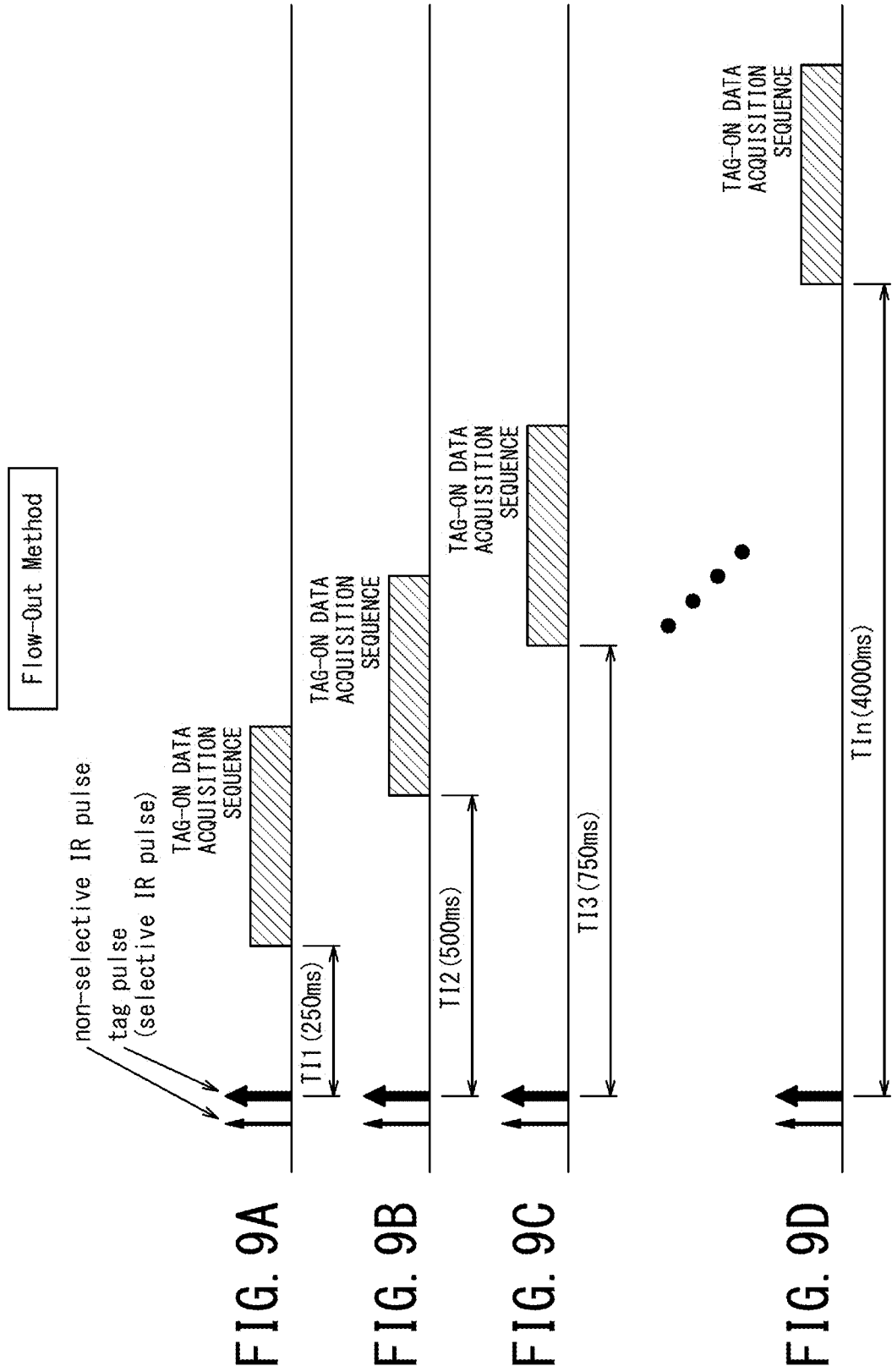

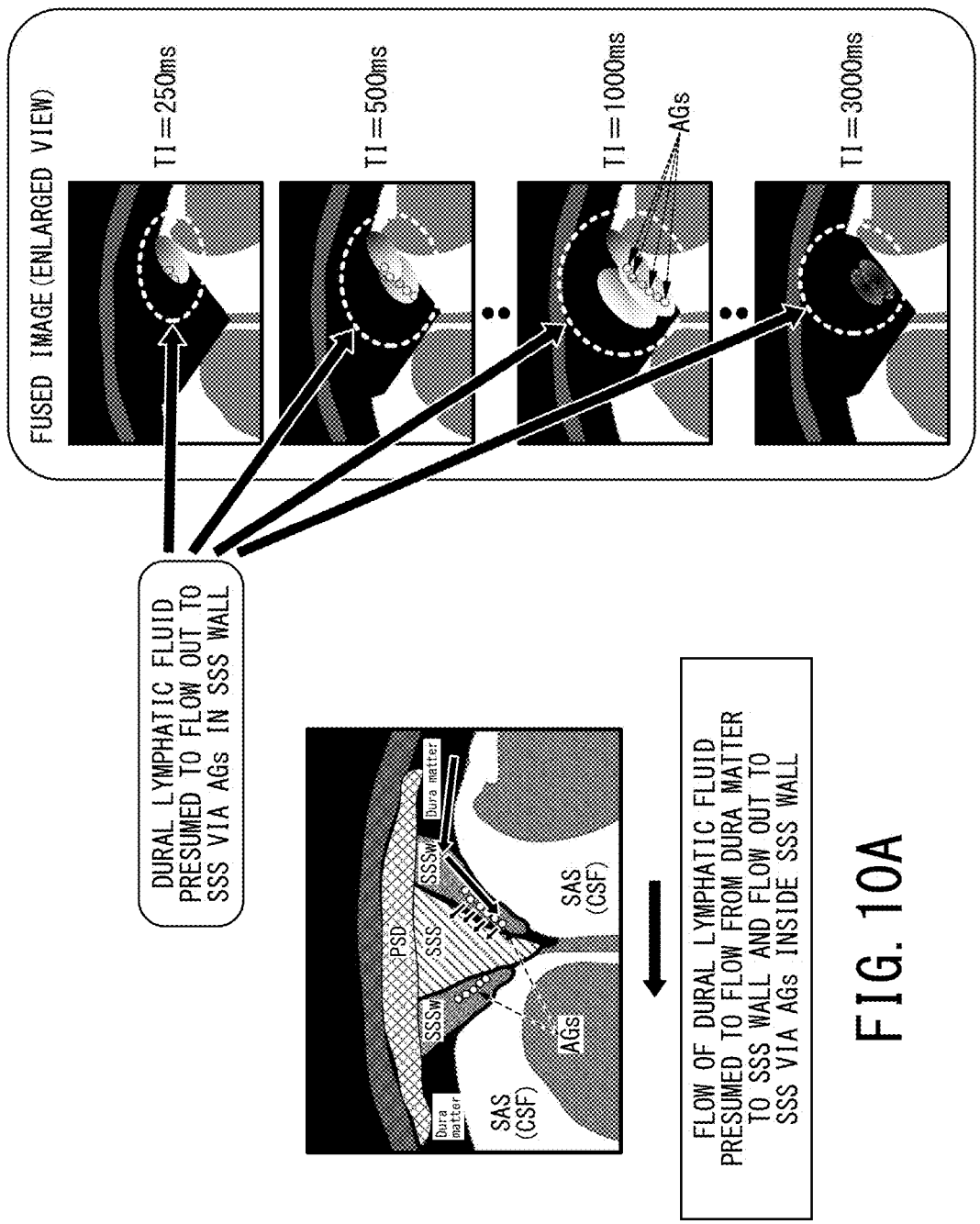

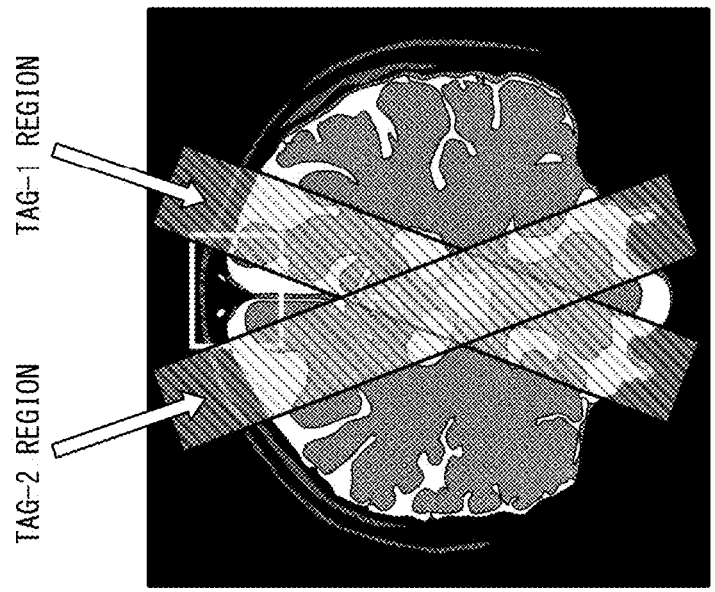
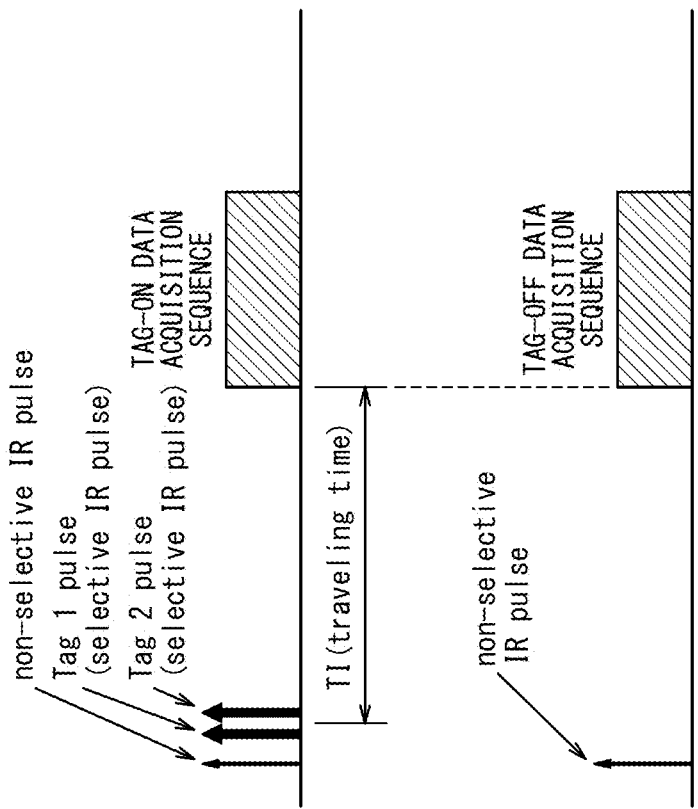
FIG. 11A
FIG. 11B
FIG. 11C

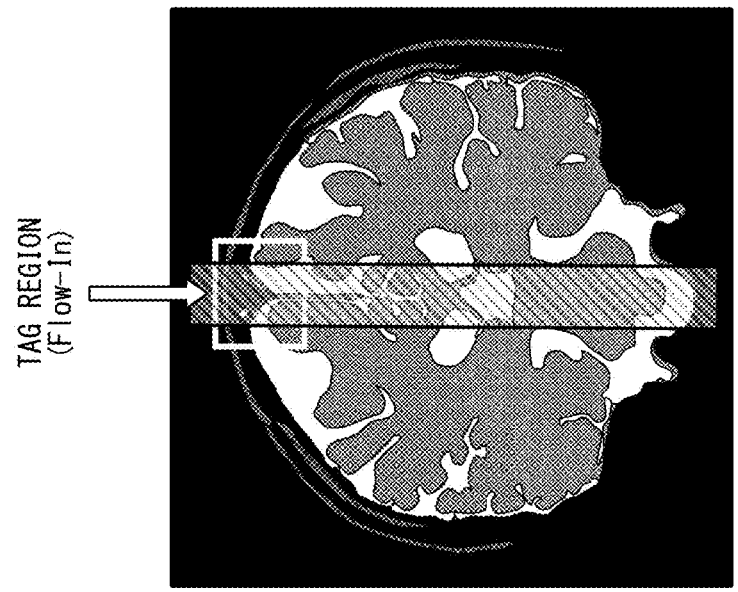
FIG. 12C
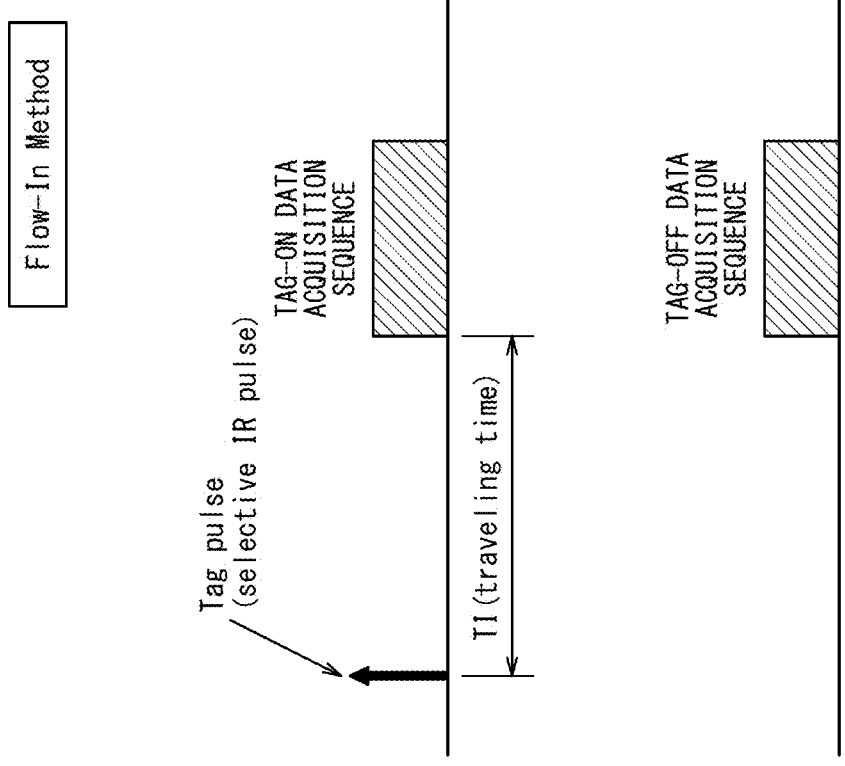
FIG. 12A
FIG. 12B

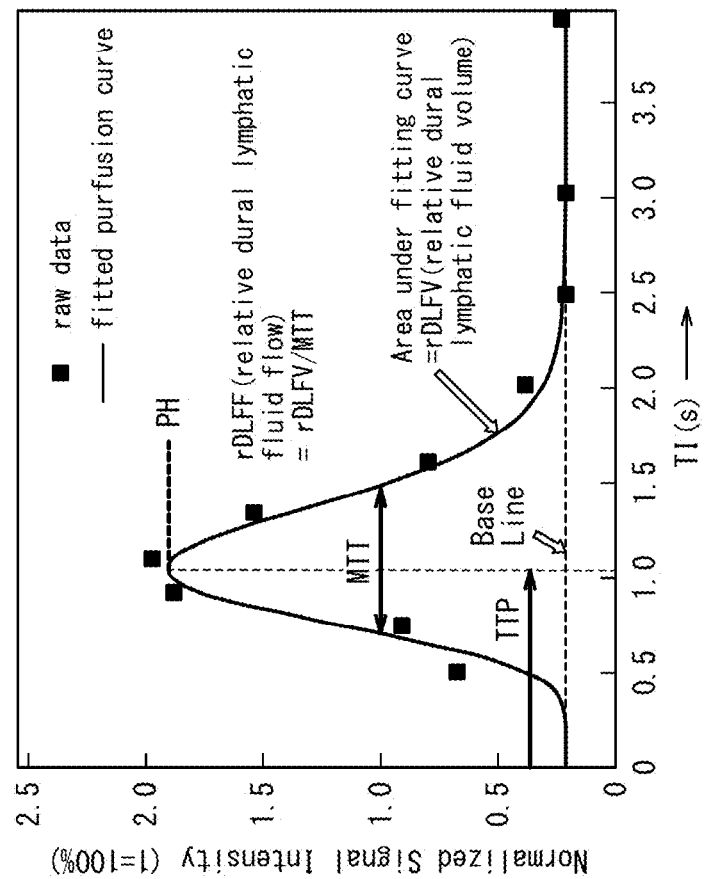
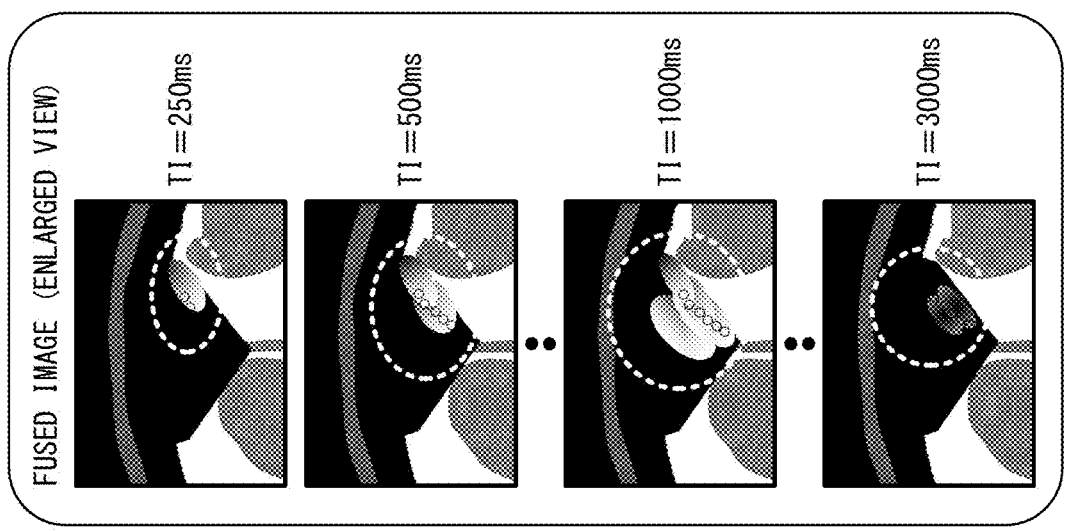
FIG. 14A
FIG. 14B

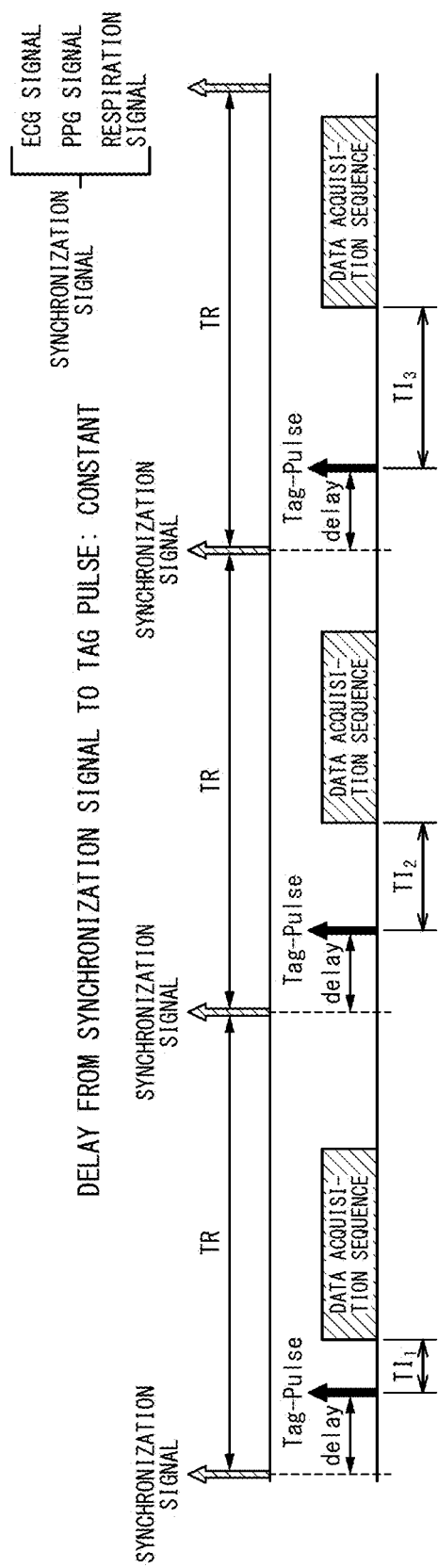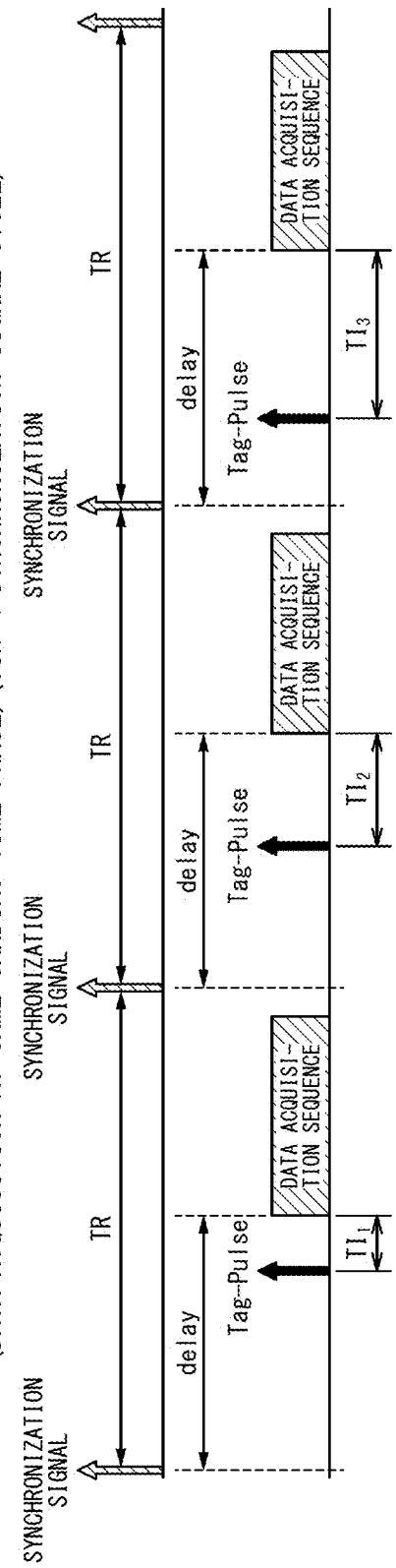

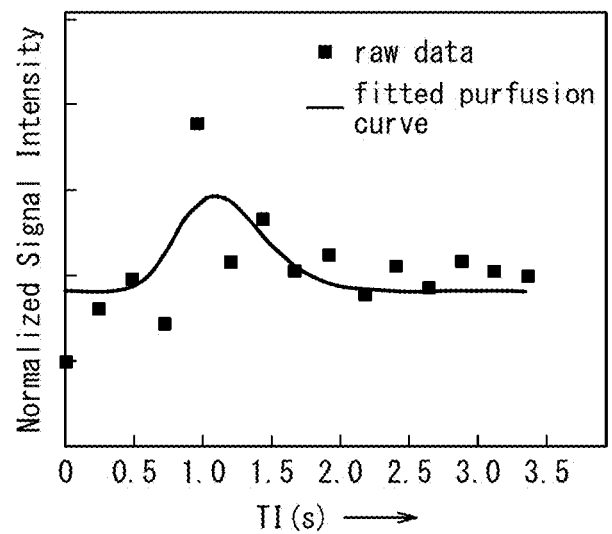
FIG. 21A (Ungated)
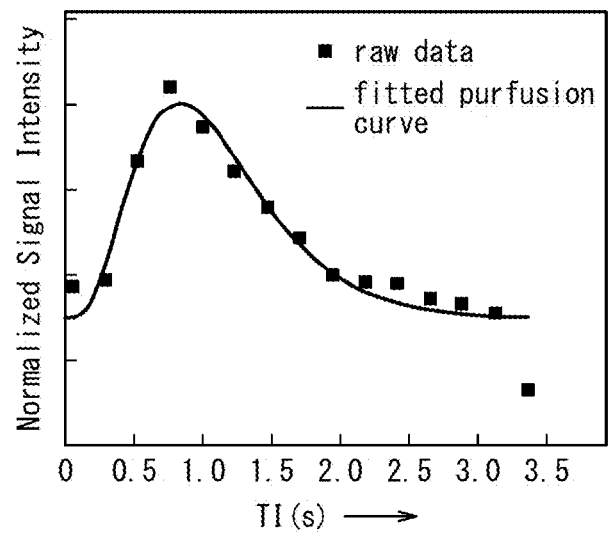
FIG. 21B (PPG gating)
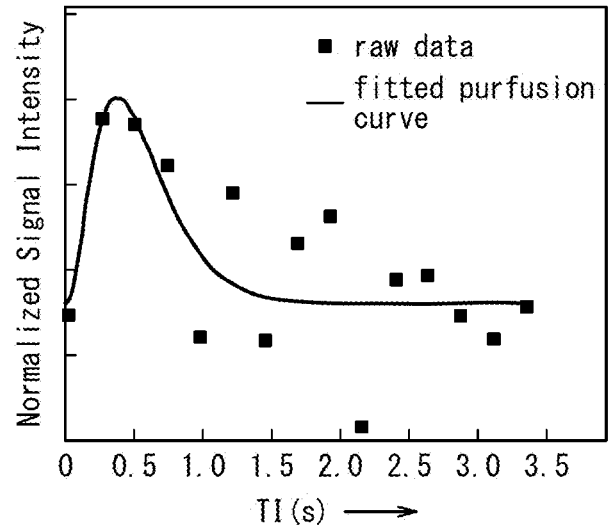
FIG. 21C (RESP gating)

MRI APPARATUS

CROSS-REFERENCE TO RELATED APPLICATIONS

This application claims the benefit of priority of U.S. Provisional Applications No. 63/308,560, filed Feb. 10, 2022, the entire contents of which are incorporated herein by reference.

TECHNICAL FIELD

Disclosed Embodiments relate to a magnetic resonance imaging (MRI) apparatus.

BACKGROUND

An MRI apparatus is an imaging apparatus which magnetically excites nuclear spin of an object placed in a static magnetic field with a radio frequency (RF) pulse having the Larmor frequency and reconstructs an image on the basis of magnetic resonance (MR) signals emitted from the object due to the excitation.

In recent years, it has come to be considered that the glymphatic system, which corresponds to the lymphatic system having a function of removing waste products, exists in the central nerve system, and cerebrospinal fluid (CSF) and/or interstitial fluid (ISF) may act as substitutes for the lymphatic fluid.

Conventionally, it has been considered that the cerebrospinal fluid and/or the interstitial fluid are produced in the choroid plexus in the cerebral ventricle, flow out from the cerebral ventricle and flow into the subarachnoid space (SAS), and are finally absorbed through the arachnoid granulation (AG) into the superior sagittal sinus (SSS) so as to enter the venous system.

Meanwhile, recent studies based on analysis of MRI images using a gadolinium-based contrast agent (also called a tracer) have shown the following suggestion. That is, dural lymphatic fluid flowing through the dural lymphatic vessels or meningeal lymphatic vessels, which lies in the parasagittal dura (PSD) along the side wall of the groove of the superior sagittal sinus, may act as the carrier of waste products in the brain.

Incidentally, the cerebrospinal fluid and/or the interstitial fluid, or the fluid around the cranial nervous system such as the dural lymphatic fluid, may be collectively called neurofluid.

The clearance (i.e., the function of removing waste products) by body fluids such as cerebrospinal fluid and dural lymphatic fluid is known to have extremely important effects on neurodegenerative diseases such as Alzheimer's disease, Parkinson's disease, and amyotrophic lateral sclerosis (ALS). Thus, it is very important for health of the human brain and tissues to elucidate the mechanism of perfusion of body fluid such as cerebrospinal fluid and dural lymphatic fluid in the brain in more detail.

As described above, conventionally, a gadolinium-based tracer (i.e., contrast agent) is intrathecally injected from the spinal cord, and the tracer in the brain is imaged by MRI to observe perfusion behavior of the dural lymphatic fluid in the brain.

Note that it takes several hours for the tracer to reach the vicinity of the superior sagittal sinus in the parietal region from the spinal cord. Additionally, it takes a long time such as 12 hours, 24 hours, and 48 hours for the tracer having stayed in the brain to disappear by metabolism.

For this reason, the examinee is burdened not only with invasive actions such as injection of the tracer from the spinal cord but also with repetition of imaging by an MRI apparatus, for example, every 12 hours in order to observe change in signal intensity of the tracer.

The conventional method using the tracer is not a method of directly observing the perfusion of cerebrospinal fluid and/or dural lymphatic fluid but a method of indirectly observing the perfusion of cerebrospinal fluid and/or dural lymphatic fluid through the tracer. The tracer is a foreign substance to the human body, and the human body tries to eliminate the foreign substance. Thus, in the indirect observation of cerebrospinal fluid and/or dural lymphatic fluid through the tracer, a natural perfusion behavior of cerebrospinal fluid and/or dural lymphatic fluid without inclusion of the foreign substance is not necessarily observed. In other words, the conventional method using the tracer is an extrinsic observation and is not an intrinsic natural observation.

Further, as described above, in the conventional imaging using the tracer, the signal intensity from the tracer is observed over a long span such as 12 hours, 24 hours, and 48 hours. Hence, it cannot be said that the conventional method observes the perfusion behavior of cerebrospinal fluid and/or dural lymphatic fluid in real time.

BRIEF DESCRIPTION OF THE DRAWINGS

In the accompanying drawings:

FIG. 9A to FIG. 9D are diagrams illustrating a tag-on pulse sequence in which a plurality of different delay time TIs are set and tag-on data are acquired for each different delay time TI;

FIG. 10A and FIG. 10B are schematic enlarged views illustrating some fused images for a plurality of delay time TIs;

FIG. 11A to FIG. 11C are diagrams illustrating a first modification of the first embodiment;

FIG. 12A to FIG. 12C are diagrams illustrating a second modification of the first embodiment.

FIG. 14A and FIG. 14B are conceptual diagrams illustrating analysis processing to be performed in the second embodiment;

FIG. 19A is a diagram illustrating a pulse sequence in which time length from a synchronization signal to a tag pulse is defined as delay time and this delay time is set to a constant value to acquire tag-on data (i.e., the same diagram as the upper part of the pulse-sequence diagram of FIG. 16);

FIG. 19B is a diagram illustrating a pulse sequence in which time length from a synchronization signal to start of acquisition of tag-on data is defined as delay time and this delay time is set to a constant value to acquire tag-on data;

FIG. 21A is a diagram illustrating raw data and a perfusion curve calculated from data that are acquired under ungated imaging;

FIG. 21B is a diagram illustrating raw data and a perfusion curve calculated from data that are acquired under PPG (peripheral pulse) gating imaging; and FIG. 21C is a diagram illustrating raw data and a perfusion curve calculated from data that are acquired under respiratory gating imaging.

DETAILED DESCRIPTION

Hereinbelow, an MRI apparatus 1 according to each embodiment of the present invention will be described by referring to the accompanying drawings.

In one embodiment, an MRI apparatus includes: a scanner that includes a static magnetic field magnet configured to generate a static magnetic field, a gradient coil configured to generate a gradient magnetic field, and a WB coil configured to apply an RF pulse to an object; and processing circuitry. The processing circuitry is configured to: cause the scanner to image, under a first imaging method, a tissue including a perfusion route of body fluid that removes waste products of the object, the body fluid including neurofluid; generate an anatomical image of the tissue from first data acquired by imaging under the first imaging method; cause the scanner to image perfusion behavior of the body fluid in real time under a second imaging method using non-contrast perfusion imaging; generate a perfusion image indicating the perfusion behavior of the body fluid from second data acquired by imaging under the second imaging method; and generate a fused image by combining the anatomical image and the perfusion image.

First Embodiment

Figure 1:
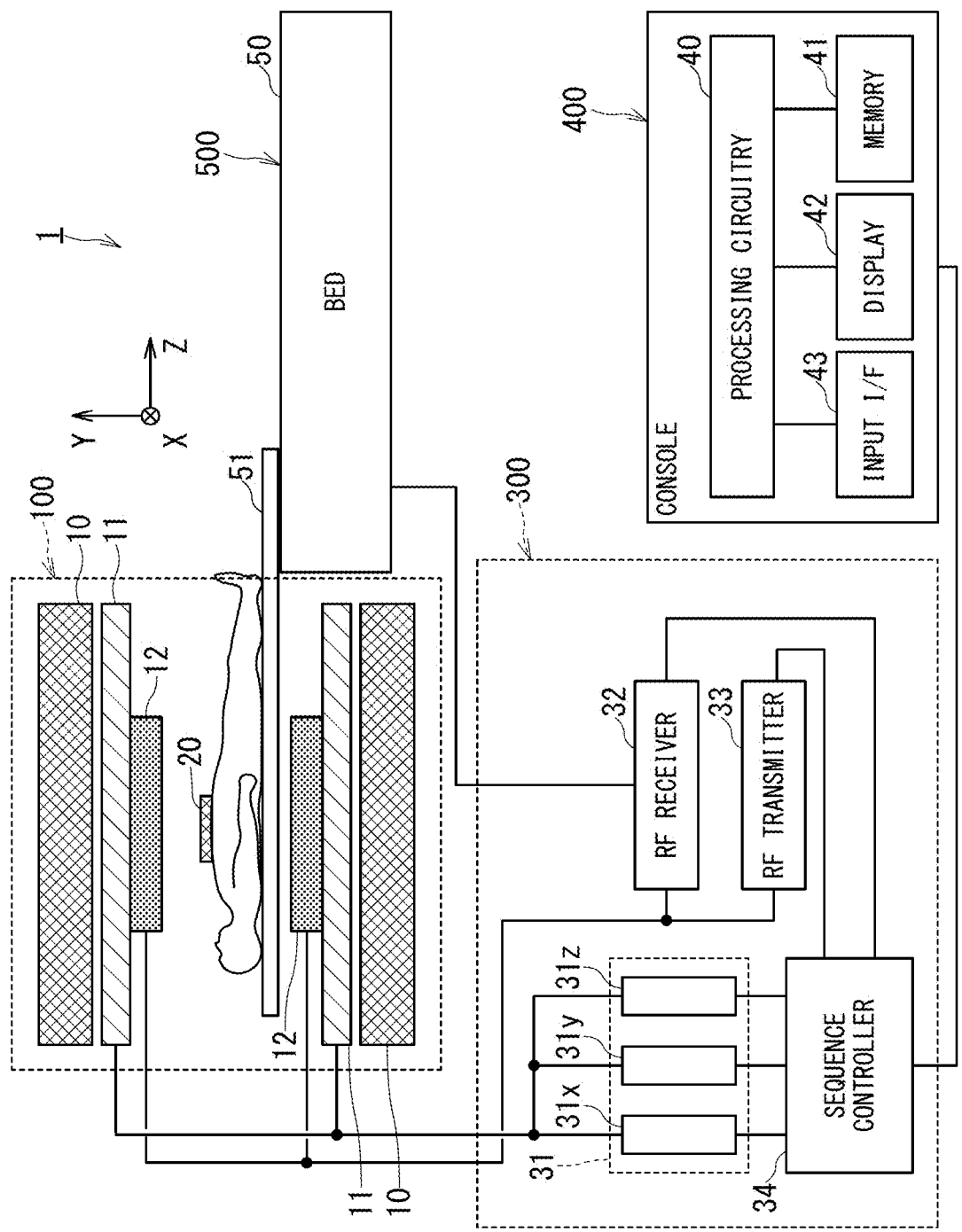
FIG. 1 is a schematic diagram illustrating an overall configuration of an MRI apparatus of one embodiment.

FIG. 1 is a block diagram illustrating the overall configuration of the MRI apparatus 1 of the first embodiment. The MRI apparatus 1 includes components such as a gantry 100, a control cabinet 300, a console 400, and a bed 500.

The gantry 100 includes, for example, a static magnetic field magnet 10, a gradient coil 11, a WB (Whole Body) coil 12, and these components are included in a cylindrical housing. The bed 500 includes a bed body 50 and a table 51.

Additionally, The MRI apparatus 1 further includes an array coil 20 that is attached near an object.

The control cabinet 300 includes gradient coil power supplies 31 (to be exact, 31x for the X-axis, 31y for the Y-axis, and 31z for the Z-axis), an RF receiver 32, an RF transmitter 33, and a sequence controller 34.

The static magnetic field magnet 10 of the gantry 100 is substantially in the form of a cylinder, and generates a static magnetic field inside the bore (i.e., the space inside the cylindrical structure of the static magnetic field magnet 10) which is an imaging region of an object (for example, a patient). The static magnetic field magnet 10 includes a superconducting coil inside, and the superconducting coil is cooled down to an extremely low temperature by liquid helium. The static magnetic field magnet 10 generates a static magnetic field by supplying the superconducting coil with electric current provided from a static magnetic field power supply (not shown) in an excitation mode. Afterward, the static magnetic field magnet 10 shifts to a permanent current mode, and the static magnetic field power supply is separated. Once it enters the permanent current mode, the static magnetic field magnet 10 continues to generate a strong static magnetic field for a long time, for example, over one year. Note that the static magnetic field magnet 10 may be configured as a permanent magnet.

The gradient coil 11 is also substantially in the form of a cylinder, and is fixed to the inside of the static magnetic field magnet 10. This gradient coil 11 applies gradient magnetic fields to an object in the respective directions of the X-axis, the Y-axis, and the Z-axis by using electric currents supplied from the gradient coil power supplies 31x, 31y, and 31z.

The bed body 50 of the bed 500 can move the table 51 in the upward and downward directions, and moves the table 51 with the object loaded thereon to a predetermined height before imaging. Afterward, at the time of imaging, the bed body 50 moves the table 51 in the horizontal direction so as to move the object inside the bore.

The WB body coil is shaped substantially in the form of a cylinder so as to surround an object, and is fixed to the inside of the gradient coil 11. The WB coil 12 applies an RF pulse transmitted from the RF transmitter 33 to the object, and receives MR signals emitted from the object due to excitation of hydrogen nuclei.

The array coil 20 is an RF coil, and receives MR signals emitted from the object at positions close to the object. The array coil 20 is, for example, configured of a plurality of coil elements. Although there are various models for the array coil 20 such as a head coil, a chest coil, a spine coil, a lower-limb coil, and a whole-body coil depending on an anatomical imaging part of the object, the array coil 20 for the chest is illustrated in FIG. 1.

The RF transmitter 33 transmits RF pulses to the WB coil 12 on the basis of commands inputted from the sequence controller 34. The RF receiver 32 receives MR signals received by the WB coil 12 and/or the array coil 20, and transmits raw data obtained by digitizing the received MR signals to the sequence controller 34.

The sequence controller 34 performs a scan of the object by driving the gradient coil power supplies 31, the RF transmitter 33, and the RF receiver 32, under the control of the console 400. When the sequence controller 34 receives the raw data from the RF receiver 32 by performing a scan, the sequence controller 34 transmits the received raw data to the console 400.

The sequence controller 34 includes processing circuitry (not shown), which is configured as hardware such as a processor configured to execute predetermined programs, a field programmable gate array (FPGA), and an application specific integrated circuit (ASIC).

The console 400 is configured as a computer including processing circuitry 40, a memory 41, a display 42, and an input I/F (interface) 43.

The memory 41 is a recording medium including a read-only memory (ROM) and a random access memory (RAM) in addition to an external memory device such as a hard disk drive (HDD) and an optical disc device. The memory 41 stores various programs to be executed by a processor of the processing circuitry 40 in addition to various data and information.

The input I/F 43 includes various devices for an operator to input various data and information, and is configured of, for example, a mouse, a keyboard, a trackball, and/or a touch panel.

The display 42 is a display device such as a liquid crystal display panel, a plasma display panel, and an organic EL panel.

The processing circuitry 40 is, for example, a circuit provided with a CPU and/or a special-purpose or general-purpose processor. The processor implements various functions described below by executing programs stored in the memory 41. The processing circuitry 40 may be configured of hardware such as an FPGA and an ASIC. The various functions described below can also be implemented by such hardware. Additionally, the processing circuitry 40 can implement the various functions by combining hardware processing and software processing based on its processor and programs.

The console 400 controls the entirety of the MRI apparatus 1 by working these components. Specifically, the console 400 receives various commands and information such as imaging conditions that are inputted by an operator such as a medical imaging technologist via the mouse and/or the keyboard of the input I/F 43. The processing circuitry 40 causes the sequence controller 34 to perform a scan on the basis of the inputted imaging conditions, and reconstructs images on the basis of the raw data transmitted from the sequence controller 34. The reconstructed images are displayed on the display 42 and stored in the memory 41.

Figure 2:
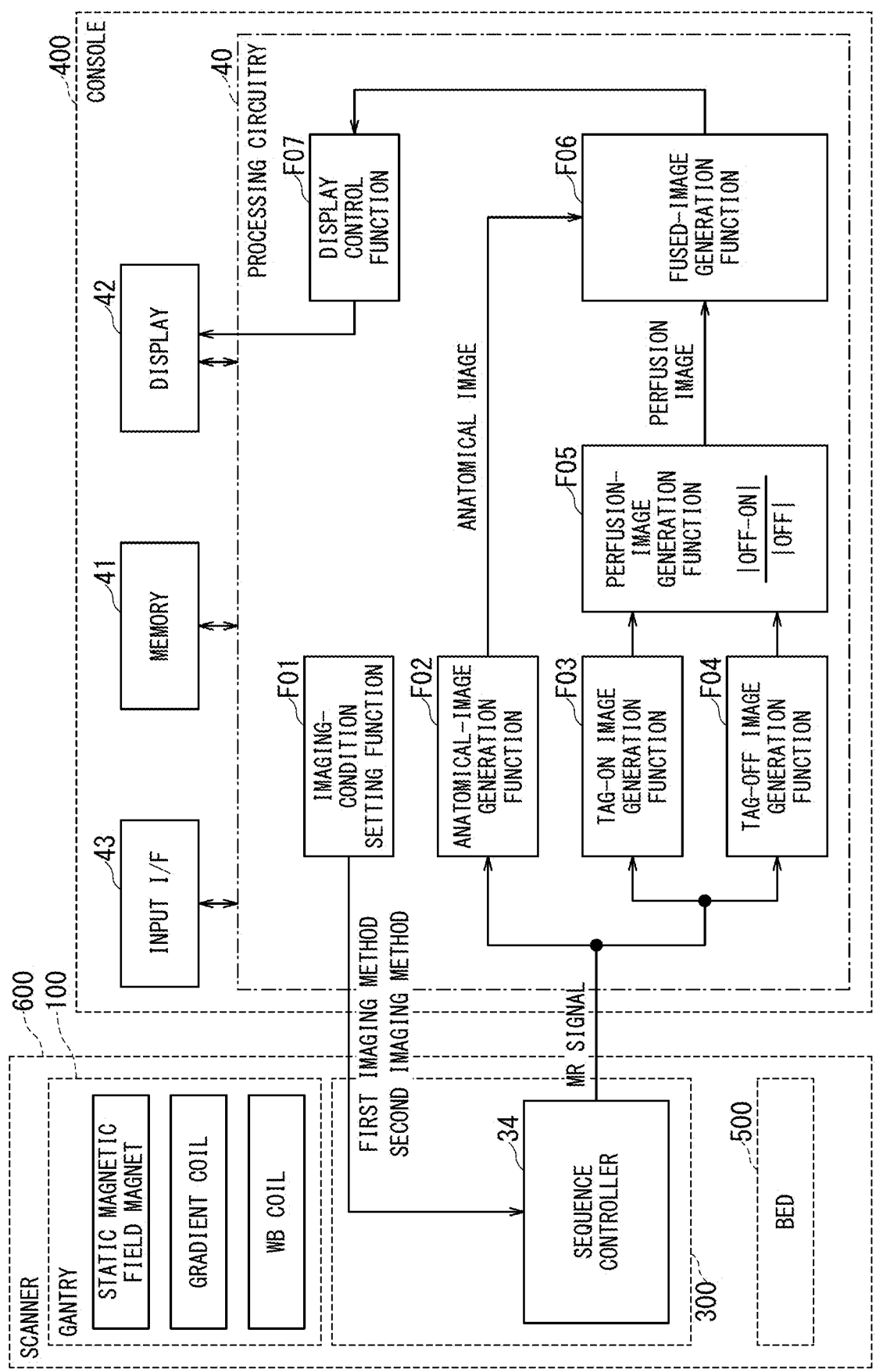
FIG. 2 is a block diagram illustrating a configuration of the MRI apparatus according to the first embodiment.

FIG. 2 is a block diagram of the MRI apparatus 1 according to the first embodiment, and, in particular, is a functional block diagram focusing on the functions to be implemented by the processing circuitry 40.

Of the components of the MRI apparatus 1 shown in FIG. 1, the components excluding the console 40 (i.e., the entirety of the control cabinet 300, the gantry 100, and the bed 500) constitute a scanner 600 as illustrated in FIG. 2.

As shown in FIG. 2, the processing circuitry 40 of the MRI apparatus 1 implements each of an imaging-condition setting function F01, an anatomical-image generation function F02, a tag-on image generation function F03, a tag-off image generation function F04, a perfusion-image generation function F05, a fused-image generation function F06, and a display control function F07.

The imaging-condition setting function F01 sets various imaging conditions on the sequence controller 34 of the scanner 600 on the basis of various data and parameters, which are related to imaging and inputted by a user such as a doctor and an imaging technologist via the input I/F 43. In the present embodiment, the imaging conditions related to the first and second imaging methods described below are set on the sequence controller 34.

The sequence controller 34 executes a pulse sequence corresponding to the selected imaging conditions so as to acquire MR signals. In detail, the sequence controller 34 acquires MR signals acquired by the pulse sequence corresponding to the first imaging method and MR signals acquired by the pulse sequence corresponding to the second imaging method.

The MR signals acquired by the first imaging method are sent to the anatomical-image generation function F02 of the processing circuitry 40. The anatomical-image generation function F02 performs reconstruction processing such as Fourier transform on the MR signals acquired by the first imaging method so as to generate an anatomical image. An anatomical image is an image in which anatomical morphology of an organ and/or tissue of an object is depicted.

The MR signals acquired by the second imaging method is sent to the tag-on image generation function F03 and the tag-off image generation function F04 of the processing circuitry 40. The second imaging method uses two pulse sequences that are a tag-on pulse sequence and a tag-off pulse sequence.

In the tag-on pulse sequence, a tag pulse is applied to a predetermined tag region, and tag-on data are acquired from a predetermined imaging region with a predetermined delay time TI from the application of the tag pulse. The tag-on image generation function F03 reconstructs the tag-on data to generate a tag-on image.

When the imaging target is fluid, the delay time TI from the application of the tag pulse to the data acquisition corresponds to time length required for the fluid to move or travel. For this reason, the delay time TI may be referred to as a traveling time TI.

In the tag-off pulse sequence, tag-off data are acquired from the predetermined imaging region (i.e., the same region as the tag-on data acquisition region) without applying the tag pulse. The tag-off image generation function F04 reconstructs the tag-off data to generate a tag-off image.

The perfusion-image generation function F05 uses the tag-on image and the tag-off image to generate a perfusion image. The fused-image generation function F06 combines the perfusion image with the anatomical image so as to generate a fused image. Details of the perfusion-image generation function F05 and the used-image generation function F06 will be described below. The generated fused image is processed by the display control function F07 into a display image for display on the display 42, and is displayed on the display 42.

Figure 3:
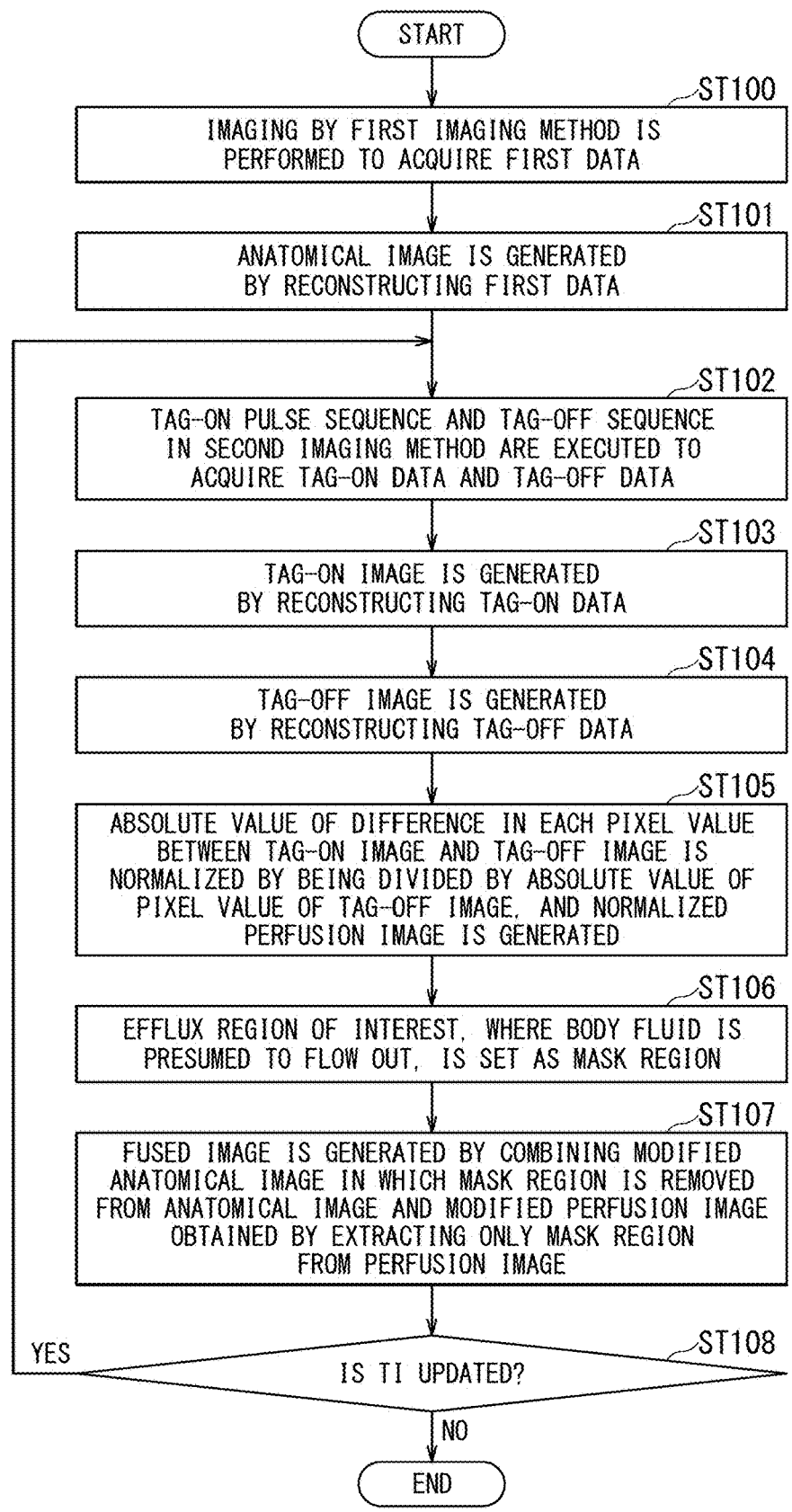
FIG. 3 is a flow chart illustrating an operation to be executed by the MRI apparatus according to the first embodiment.

FIG. 3 is a flow chart illustrating an operation to be executed by the MRI apparatus 1 according to the first embodiment. Hereinafter, the operation of the MRI apparatus 1 will be described in detail on the basis of the flowchart of FIG. 3 by using FIG. 4A to FIG. 12C.

First, in the step ST100 of FIG. 3, imaging by the first imaging method is performed and the first data are acquired.

In the next step ST101, an anatomical image is generated by reconstructing the first data.

Figure 4B:
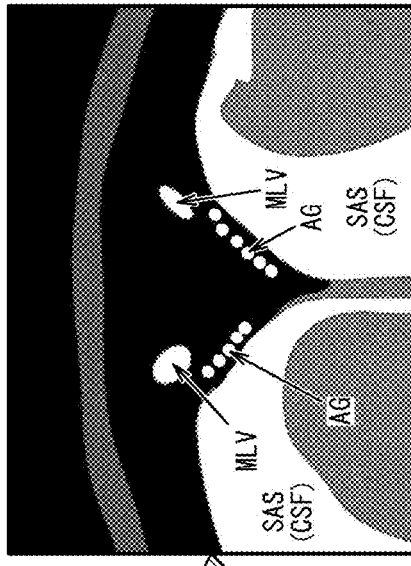
FIG. 4A to FIG. 4C are diagrams illustrating a typical anatomical image generated by the MRI apparatus.
Figure 4C:
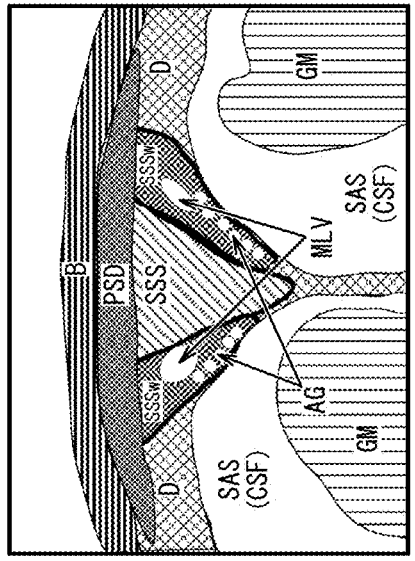
Figure 4A:
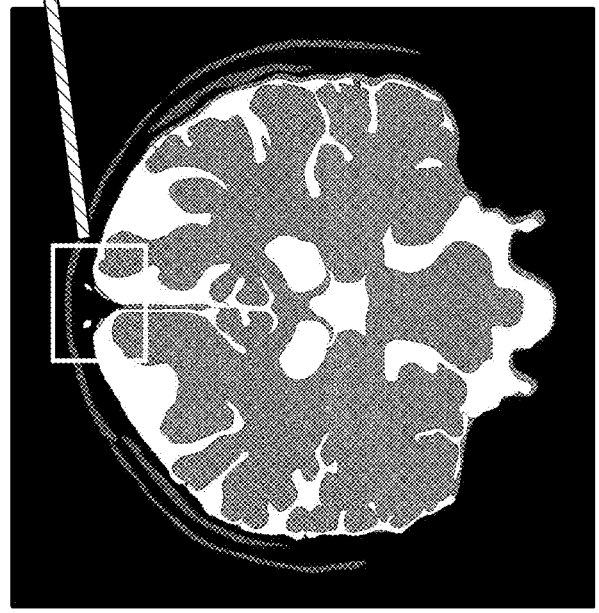

FIG. 4A is a diagram illustrating a typical anatomical image to be generated by the MRI apparatus 1 and is a coronal image of the head of the object.

As described above, an anatomical image is an image in which anatomical morphology of an organ and/or tissue of an object is depicted. The MRI apparatus 1 of the present embodiment aims to image and visualize the perfusion behavior of the body fluid, which is responsible for removing the waste products of the object, by a non-contrast perfusion imaging method that is the second imaging method. In the perfusion image generated by the second imaging method, while the perfused body fluid is satisfactorily visualized, the background around the perfused body fluid is suppressed, and thus, the position of the perfused body fluid is not always clearly identifiable. To solve this problem, the anatomical image is used for clearly identifying the position of the perfused body fluid by aligning and combining the anatomical image and the perfusion image.

Hence, it is preferred that the imaging region of the anatomical image approximately matches the imaging region of the perfusion image. In other words, when the imaging target of the non-contrast perfusion imaging method, which is the second imaging method, is the perfusion of the body fluid responsible for removing the waste products of the object, the anatomical image depicts the area that includes the tissue containing the perfusion route of this body fluid.

In particular, when the imaging target of the non-contrast perfusion imaging method (i.e., second imaging method) is dural lymphatic fluid or cerebrospinal fluid (CSF) that flows out from the subarachnoid space (SAS) on the parietal region to the wall of the superior sagittal sinus (SSSw) and/or the parasagittal dura (PSD) near the wall of the superior sagittal sinus, or flows out to the superior sagittal sinus (SSS) via the wall of the superior sagittal sinus, the anatomical image is desirably an image that depicts the area containing the subarachnoid space (SAS), the superior sagittal sinus (SSS), the wall of the superior sagittal sinus, and the parasagittal dura (PSD) near the wall of the superior sagittal sinus, as shown in FIG. 4B.

FIG. 4B is an enlarged view of the parietal region of the anatomical image shown in FIG. 4A, and FIG. 4C is a diagram conceptually illustrating the structure of human tissues in the region corresponding to the enlarged view of the parietal region of FIG. 4B.

The type of pulse sequence of the first imaging method is not limited to a specific one. For example, a pulse sequence of three-dimensional SS (single shot) FSE (Fast spin echo), such as 3D-MVOX (multi-voxel) or 3D-FASE (fast asymmetric spin echo), can be used for the pulse sequence of the first imaging method.

In terms of identifying the respective positions of the superior sagittal sinus (SSS) and the parasagittal dura (PSD) near the wall of the superior sagittal sinus, it is preferred to use a pulse sequence that can hyperintensely depict cerebrospinal fluid (CSF), which is the body fluid existing in the subarachnoid space (SAS) in the vicinity of these tissues.

Returning to FIG. 3, in the step ST102, the tag-on pulse sequence and the tag-off sequence in the second imaging method are executed such that the tag-on data and the tag-off data are acquired. The tag-on data and tag-off data are acquired approximately at the same time or substantially simultaneously.

Figures 5A, 5B:
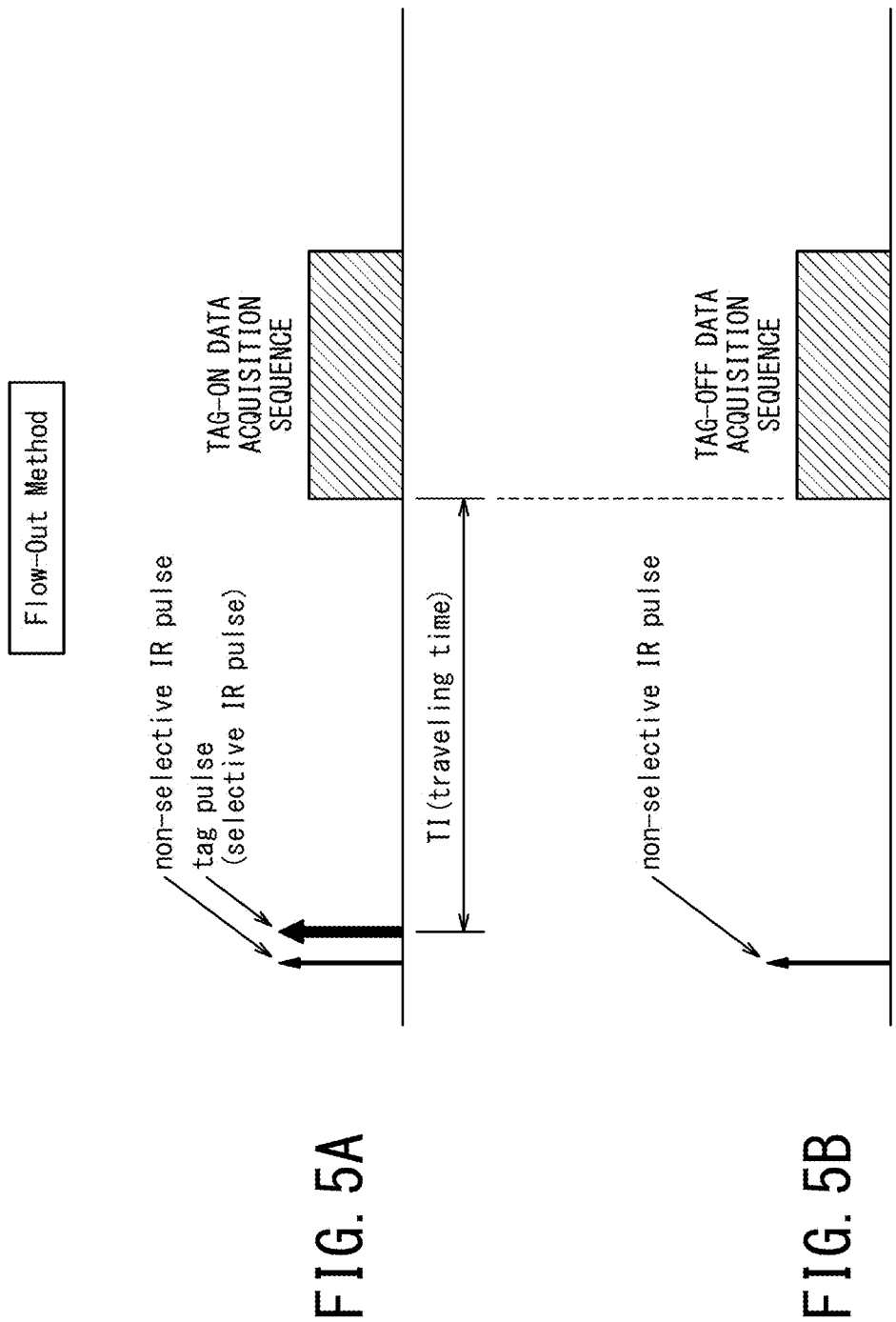
FIG. 5A is a diagram illustrating a tag-on pulse sequence.
FIG. 5B is a diagram illustrating a tag-off pulse sequence.

FIG. 5A is a diagram illustrating a tag-on pulse sequence. The tag-on pulse sequence is a pulse sequence including a tag pulse. In the tag-on pulse sequence, for example, subsequent to a region non-selective IR pulse, a tag pulse is applied as a region selective IR pulse, and a tag-on data acquisition sequence is applied after elapse of the delay time TI (or travel time TI) from the tag pulse.

FIG. 5B is a diagram illustrating a tag-off pulse sequence. The tag-off pulse sequence is a sequence in which the same region non-selective IR pulse as the tag-on pulse sequence is applied for suppressing the background, but does not include the tag pulse. The tag-off data acquisition sequence is applied at a timing at which its delay time matches the delay time of the tag-on data acquisition sequence.

By continuously applying the tag-on pulse sequence and the tag-off pulse sequence to the object, the tag-on data and the tag-off data can be acquired at the same time.

Figures 6A, 6B:
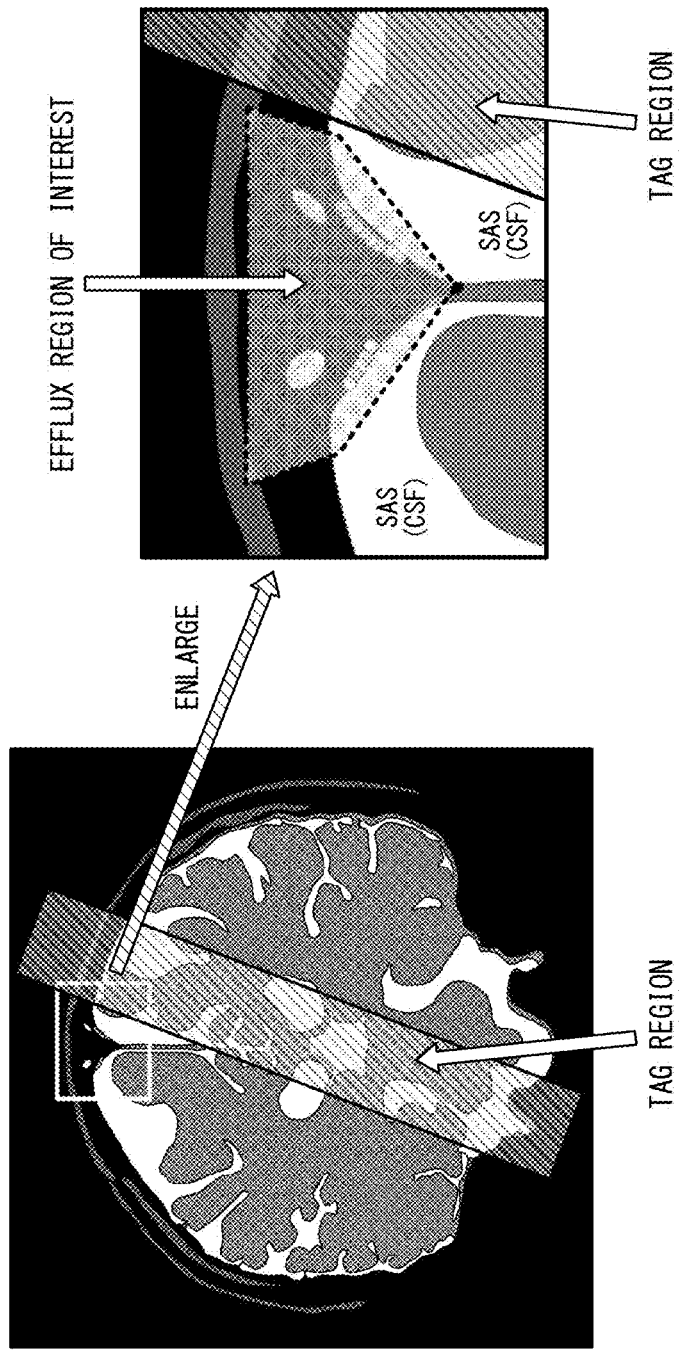
FIG. 6A and FIG. 6B are diagrams illustrating a tag region and an imaging region in a tag-on pulse sequence.

FIG. 6A and FIG. 6B are schematic diagrams illustrating a tag region (i.e., region to which the tag pulse is applied) and an imaging region (i.e., region to which the tag-on data acquisition sequence is applied) in a tag-on pulse sequence. FIG. 6B is an enlarged view of the area surrounded by the white square in the upper part of FIG. 6A.

The perfusion imaging method of the present embodiment is roughly classified into a Flow-Out method and a Flow-In method. The Flow-Out method is an imaging method that visualizes the body fluid flowing out of the tag region to the outside of the tag region, while the Flow-In method is an imaging method that visualizes the body fluid flowing into the tag region from the outside of the tag region. The respective tag regions shown in FIG. 6A and FIG. 6B correspond to the Flow-Out method.

In the Flow-Out method of the present embodiment as shown in the enlarged view of FIG. 6B, a region where the body fluid is presumed to flow out is set as an "efflux region of interest". Then, a region is set as the tag region, through which body fluid flows, and which is close to the efflux region of interest without including the efflux region of interest. Since the tag region is set in the above manner, a perfusion image can be generated as a flow-out image in which the efflux of the body fluid from the tag region to the efflux region of interest is depicted.

In particular, when the imaging target is the dural lymphatic fluid, the dural lymphatic fluid is presumed to flow from the dura mater to a wall (SSSw) of the superior sagittal sinus (SSS), and then flow out to the superior sagittal sinus (SSS) via the arachnoid granules (AG) in the wall (SSSw) of the superior sagittal sinus (SSS). In this case, as shown in the enlarged view of FIG. 6B, it is preferred to set the efflux region of interest as a region that includes the superior sagittal sinus (SSS), the wall (SSSw) of the superior sagittal sinus (SSS), and the parasagittal dura (PSD) but includes as little subarachnoid space (SAS) as possible.

The tag region is, for example, a rectangular parallelepiped three-dimensional region that has a rectangular cross-section of a coronal plane as shown in FIG. 6A and has depth in the direction perpendicular to this page.

On the other hand, the imaging region may be a two-dimensional slice region including the entire coronal cross-section of the brain as shown in FIG. 6A, or may be a three-dimensional slab region that includes the entire coronal cross-section of the brain and has predetermined thickness in the direction perpendicular to this page.

Although it is preferred that the tag-off data acquisition sequence and the tag-on data acquisition sequence are basically the same type of pulse sequence, the tag-off data acquisition sequence and the tag-on data acquisition sequence are not limited to a specific type of sequence. When the imaging region is a two-dimensional slice region, the tag-off data acquisition sequence and the tag-on data acquisition sequence may be 2D-FSE (two-dimensional Fast Spin Echo) or 2D-EPI (two-dimensional Echo Planar Imaging), for example. When the imaging region is a three-dimensional slab region, the tag-off data acquisition sequence and the tag-on data acquisition sequence may be 3D-FSE or 3D-EPI, for example.

Returning to FIG. 3, in the step ST103, a tag-on image is generated by reconstructing the acquired tag-on data.

In the step ST104, a tag-off image is generated by reconstructing the acquired tag-off data.

In the next step ST105, at the same pixel positions between the tag-on image and the tag-off image, the absolute value of difference in pixel value between the tag-on image and the tag-off image is normalized by being divided by the absolute value of the pixel value of the tag-off image, and the obtained normalized pixel values are used for generating a perfusion image.

Figure 7C:
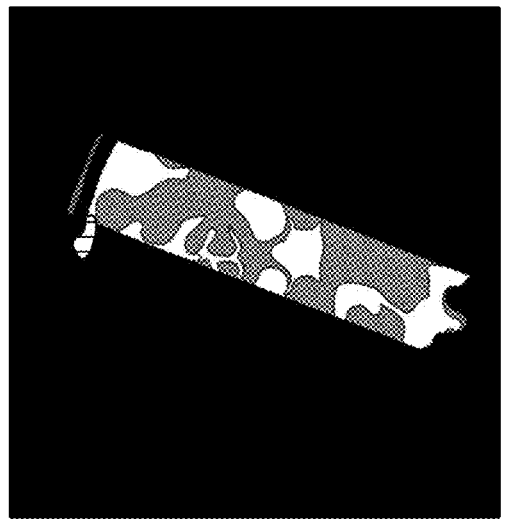
FIG. 7C is a diagram illustrating a perfusion image.
Figure 7B:
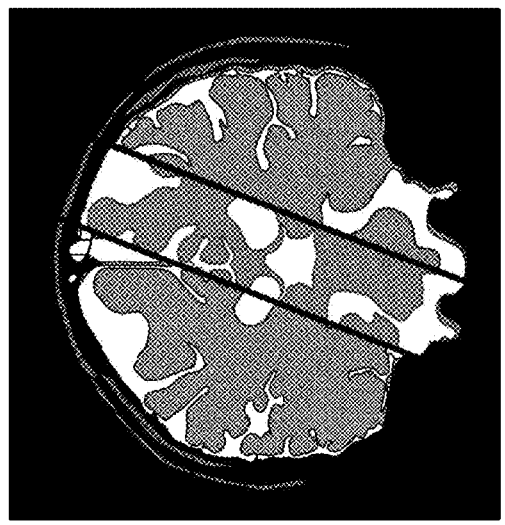
FIG. 7B is a diagram illustrating a tag-on image.
Figure 7A:
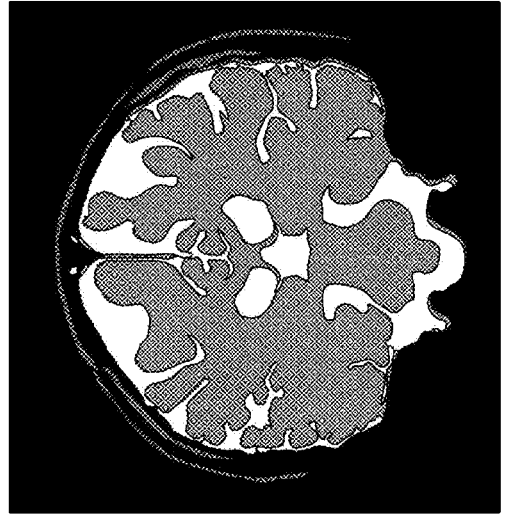
FIG. 7A is a diagram illustrating a tag-off image.

FIG. 7A to FIG. 7C are diagrams illustrating the concept of the processing from the steps ST103 to ST105. In detail, FIG. 7A is a schematic diagram illustrating a tag-off image generated in the step ST104, FIG. 7B is a schematic diagram illustrating a tag-on image generated in the step ST103, and FIG. 7C is a schematic diagram illustrating a perfusion image generated in the step ST105.

When each pixel value of the tag-off image and each pixel value of the tag-on image are respectively defined as IM(OFF) and defined IM(ON) at the same pixel positions between both images, each pixel value IM(perfusion) of the perfusion image is calculated by Expression 1 below, as shown at the bottom of FIG. 7A to FIG. 7C.

$$IM(\text{perfusion}) = |IM(\text{OFF}) - IM(\text{ON})| / |IM(\text{OFF})| \quad \text{Expression 1}$$

Since the tag-off image and the tag-on image are almost the same in pixel value in the region that is outside the tag region and includes no movement, in the perfusion image generated as the difference between the tag-off image and the tag-on image, each pixel value is small outside the tag-on region. Thus, in the perfusion image shown in FIG. 7C, the outside of the tag region is depicted in black.

On the other hand, the pixel value of the body fluid having flowed out of the tag region during the period from the application time of the tag pulse to the elapse of the delay time TI is not cancelled by the difference between the tag-off image and the tag-on image. Thus, the body fluid having flowed out of the tag region is brightly depicted in the perfusion image as illustrated in the upper small part of FIG. 7C.

Next, in the step ST106, the efflux region of interest, where the body fluid is presumed to flow out, is set as the mask region.

In the step ST107, a fused image is generated by combining the anatomical image after masking (i.e., modified anatomical image obtained by eliminating the mask region from the anatomical image) and the perfusion image after masking (i.e., modified perfusion image obtained by extracting only the mask region from the perfusion image).

Figure 8:
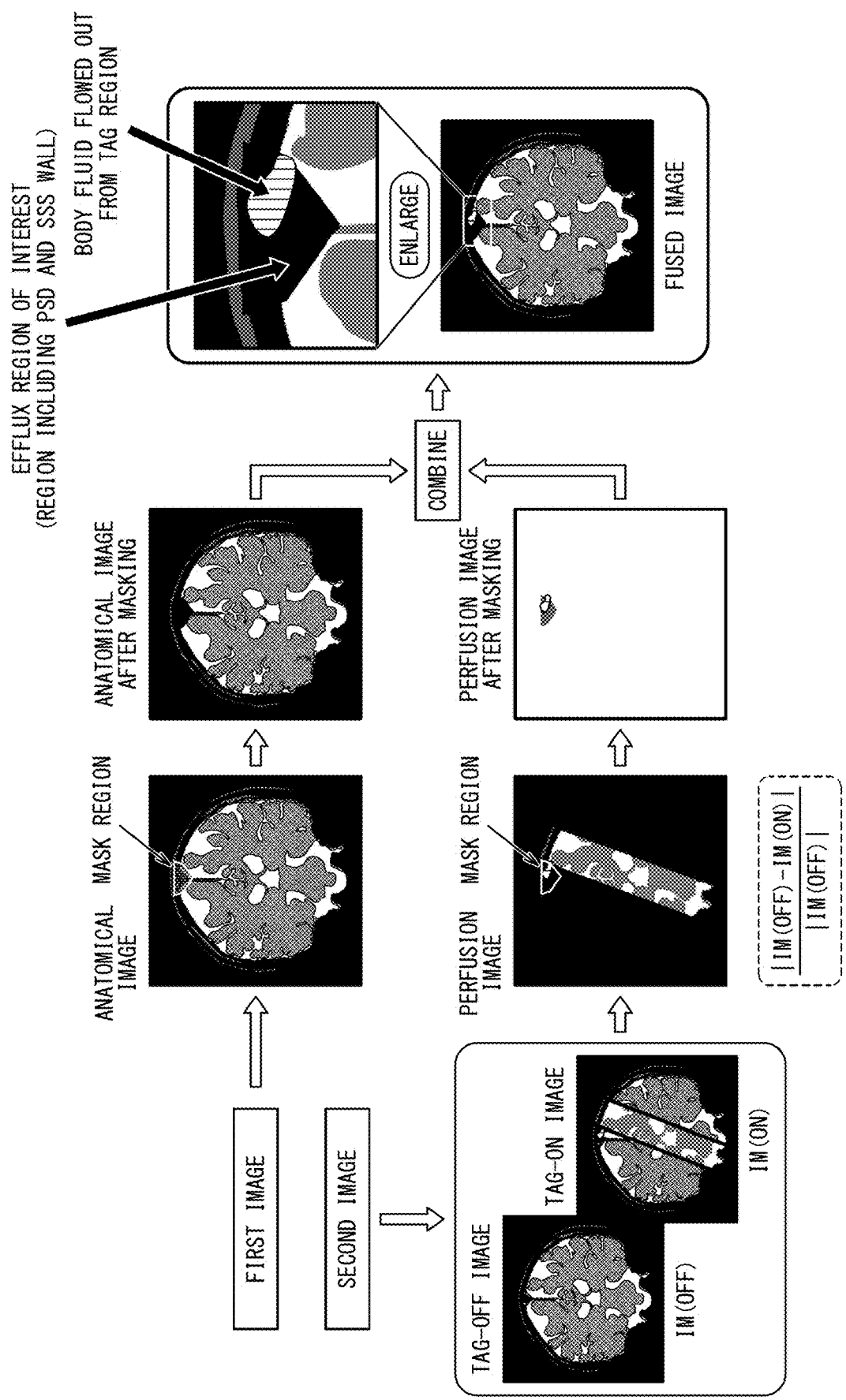
FIG. 8 is a diagram illustrating the concept of the entire processing from the steps ST100 to ST107 in FIG. 3.

FIG. 8 is a diagram illustrating the concept of the entire processing from the steps ST100 to ST107 including the above-described steps ST106 and ST107. The upper part of FIG. 8 shows the flow of the processing for generating the anatomical image after masking in which the mask region is removed from the anatomical image obtained in the first imaging.

The lower part of FIG. 8 shows the flow of the processing for generating the perfusion image from the tag-on image and the tag-off image obtained in the second imaging and further generating the perfusion image after masking. In the perfusion image after masking, the regions excluding the mask region are removed from the perfusion image.

The rightmost part of FIG. 8 illustrates the fused image generated by combining the anatomical image after masking and the perfusion image after masking and also illustrates an enlarged view of this fused image.

The fused image clearly depicts the body fluid having flowed out of the tag region, together with the tissue structure of both of the efflux region of interest into which the body fluid flows, and its surrounding region. Thus, by setting the efflux region of interest to a region including the superior sagittal sinus (SSS), the wall (SSSw) of the superior sagittal sinus (SSS), and the parasagittal dura (PSD), the perfusion behavior of the dural lymphatic fluid, which is presumed to flow out of the tag region and flow out through the wall (SSSw) of the superior sagittal sinus (SSS), can be clearly depicted together with a efflux position.

So far, a description has been given of the processing flow of generating the perfusion image with respect to one delay time TI. However, the MRI apparatus 1 of the present embodiment can also generate a plurality of perfusion images for a plurality of different delay time TIs.

FIG. 9A to FIG. 9D are diagrams illustrating tag-on pulse sequences in which a plurality of different delay time TIs are set, and the tag-on data are acquired for each different delay time TI. Although not shown, a plurality of tag-off pulse sequences corresponding to the respective tag-on pulse sequences are performed to acquire a plurality of tag-off data corresponding to the different delay time TIs.

The plurality of tag-on data and the plurality of tag-off data acquired in the above manner are used for generating respective perfusion images corresponding to the different delay time TIs. Further, respective fused images corresponding to different delay time TIs are generated by combining the generated perfusion images with one anatomical image having already been generated.

In the step ST108 of FIG. 3, it is determined whether the delay time TIs are updated or not. The delay time TI may be updated by using a plurality of predetermined delay time TIs or may be sequentially increased from the initial value (i.e., delay time $TI_0$) by a predetermined step size ($\delta TI$).

The processing from the steps ST102 to ST107 is repeated for all the delay time TIs, and thereby, respective fused images for all the delay time TIs are generated.

FIG. 10A and FIG. 10B are schematic diagrams illustrating respective enlarged views of some fused images for a plurality of delay time TIs that are set to stepwisely increase from 250 ms to 3000 ms in increments of 250 ms, for example.

As shown in FIG. 10A, the dural lymphatic fluid is presumed to flow from the dura mater to the wall of the superior sagittal sinus (SSSw) and then flow out via the arachnoid granules (AGs) in the wall of the superior sagittal sinus (SSSw) into the superior sagittal sinus (SSS). FIG. 10B illustrates images that are generated in order to visualize the perfusion behavior of such dural lymphatic fluid.

FIG. 10B illustrates the following perfusion behavior of the dural lymphatic fluid. That is, the amount of the dural lymphatic fluid having flowed out of the tag region, or intensity of the signal from the dural lymphatic fluid, gradually increases with elapse of the delay time TI from, for example, a delay time TI=250 ms, then reaches a maximum at around a delay time TI=1000 ms, and after that, gradually decreases.

As mentioned above, conventionally, the perfusion behavior of body fluid such as dural lymphatic fluid is obtained under invasive imaging by using a tracer (i.e., contrast medium) over a long period of time such as 12 hours, 24 hours, and 48 hours. By contrast, the MRI apparatus 1 according to the first embodiment can visualize such perfusion behavior of body fluid in real time under non-invasive imaging without using a tracer (i.e., contrast medium).

Modifications of First Embodiment

FIG. 11A to FIG. 11C are diagrams illustrating a first modification of the first embodiment. In the first modification, as shown in FIG. 11C, a plurality of tag regions (for example, two tag regions including a tag-1 region and a tag-2 region) are set. Such setting enables generation of a perfusion image that depicts the body fluid flowing out from the plurality of tag regions into the efflux region of interest in a plurality of directions. Note that, even in this imaging method, the body fluid flowing out from the tag regions is depicted. Thus, this imaging method belongs to the Flow-Out method similarly to the first embodiment, and the perfusion image generated by this imaging method is a Flow-Out image.

The plurality of tag regions are set by differentiating the respective application regions of the plurality of (for example, two) tag pulses, which are applied immediately after the non-selective IR pulse as shown in FIG. 11A.

FIG. 12A to FIG. 12C are diagrams illustrating a second modification of the first embodiment. In the first embodiment and its first modification described so far, each tag region is set outside the efflux region of interest. By contrast, in the second modification, as shown in FIG. 12C, the tag region is set in the efflux region of interest, which includes the superior sagittal sinus (SSS), the wall (SSSw) of the superior sagittal sinus (SSS), and the parasagittal dura (PSD).

In the second modification, the body fluid flowing from the outside of the tag region into the tag regions, which are the efflux region of interest, is depicted. Thus, this imaging method is called a Flow-In method, and the perfusion image generated by the Flow-In method is a Flow-In image.

The tag region of the Flow-In method is set by the application region of the tag pulse of the region-selective IR pulse as shown in FIG. 12A.

Each pixel value IM(perfusion) of the perfusion image in the Flow-In method is calculated by the following Expression 2, which is substantially the same as Expression 1 described above.

$$IM(\text{perfusion}) = |IM(\text{ON}) - IM(\text{OFF})|/|IM(\text{OFF})| \quad \text{Expression 2}$$

Wherein, at the same pixel positions, each pixel value of the perfusion image is expressed as IM(perfusion), each pixel value of the tag-off image is expressed as IM(OFF), and each pixel value of the tag-on image is expressed as IM(ON).

Second Embodiment

Figure 13:
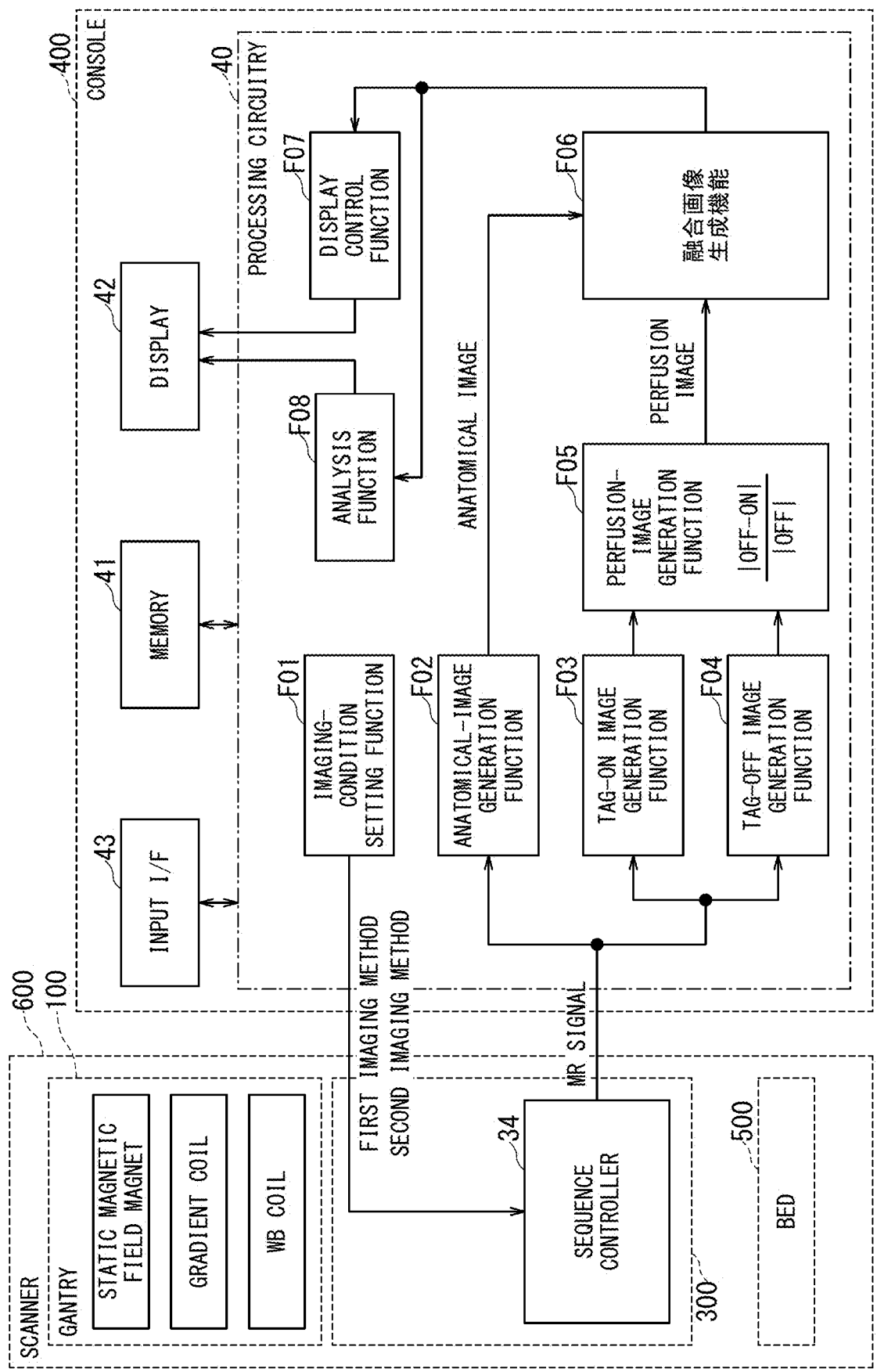
FIG. 13 is a block diagram illustrating a configuration of the MRI apparatus according to the second embodiment.

FIG. 13 is a block diagram illustrating a configuration of the MRI apparatus 1 according to the second embodiment. The difference between the first and second embodiments is that the MRI apparatus 1 of the second embodiment further includes an analysis function F08.

FIG. 14A and FIG. 14B are conceptual diagrams illustrating analysis processing implemented by the analysis function F08. From a plurality of fused images (or a plurality of perfusion images) having different delay time TIs shown in FIG. 14A, specific pixel values in the efflux region of interest including the wall of the superior sagittal sinus (SSSw) are extracted in this analysis processing, for example. A perfusion curve as shown in FIG. 14B is calculated from the extracted plurality of specific pixel values and the plurality of delay time TIs corresponding to the respective specific pixel values.

The perfusion curve can be calculated by curve-fitting the plurality of extracted specific pixel values and the plurality of the delay time TIs corresponding to the respective specific pixel value to a predetermined curve.

The above-described predetermined curve is, for example, a curve defined by a gamma variate function represented by Expression 3 below.

$$y = p1 \cdot (TI)^{p2} \cdot \exp[-(TI)/p3] + p4 \quad \text{Expression 3}$$

In Expression 3, TI is the delay time TI. Further, p1, p2, p3, and p4 are constants.

In order to calculate the above-described predetermined curve by curve-fitting, it is preferred to use at least four different delay time TIs and at least four pixel values corresponding to the respective delay time TIs, for example.

In particular, when the target body fluid for which perfusion behavior is observed is the dural lymphatic fluid, the peak position of the perfusion curve is typically presumed to be at a delay time TI of approximately 1.2 seconds. Thus, the plurality of delay time TIs to be used for curve-fitting are desirably set as respective positions of a total of at least six points, which includes: one point between 0.4 seconds and 0.6 seconds in the presumed rising region of the perfusion curve; one point between 0.8 seconds and 1.16 seconds; one point between 1.2 seconds and 1.5 seconds near the peak; one point between 1.5 seconds and 2.0 seconds; and two points after 2.5 seconds in the period estimated to be after the falling region of the perfusion curve.

In FIG. 14B illustrating the perfusion curve, the horizontal axis indicates the delay time TI and the vertical axis indicates normalized signal intensity. The normalized signal intensity is a relative value calculated by Expression 1 or Expression 2, and the value "1.0" of this normalized signal intensity corresponds to 100%.

The analysis function F08 can calculate some more useful perfusion indexes from the perfusion curve estimated in the above manner.

For example, when the body fluid to be perfused is the dural lymphatic fluid, the estimated perfusion curve enables calculation of at least one of: a peak height PH which indicates the value of the peak of the curve; a time from the application of the tag pulse to the arrival of the peak, i.e., time to peak TTP; a mean transition time (MTT) of the perfused dural lymphatic fluid; rDLFV (relative dural lymphatic fluid volume) indicating the relative volume of the perfused dural lymphatic fluid; and rDLFF (relative dural lymphatic fluid flow) indicating the relative flow rate of the perfused dural lymphatic fluid.

The relative volume (rDLFV) of the dural lymphatic fluid can be determined by calculating the area of the region between the perfusion curve and the baseline. The relative flow rate (rDLFF) of the dural lymphatic fluid can be determined by dividing the relative volume of the dural lymphatic fluid by the mean transition time MTT. The perfusion behavior of the dural lymphatic fluid can be quantitatively determined from the respective calculated indexes.

The perfusion curve can be calculated from any one of a two-dimensional perfusion image and a three-dimensional perfusion image.

Other analysis implemented by the analysis function F08 includes processing of calculating virtual flow velocity of body fluid such as the dural lymphatic fluid.

For example, a plurality of difference images are obtained by the difference between one reference perfusion image (or one reference fused image) having the reference delay time TI and plural perfusion images (or plural fused images) having different delay time TIs. Then, the virtual flow velocity of the body fluid can be calculated from the change in spread of the region of the body fluid ($\Delta x$) depicted in the difference images and the increment of the delay time TI ($\Delta TI$). Alternatively, a plurality of difference images may be obtained by calculating the difference between two perfusion images (or fused images) having closest delay time TIs for each delay time TI.

Figure 15:
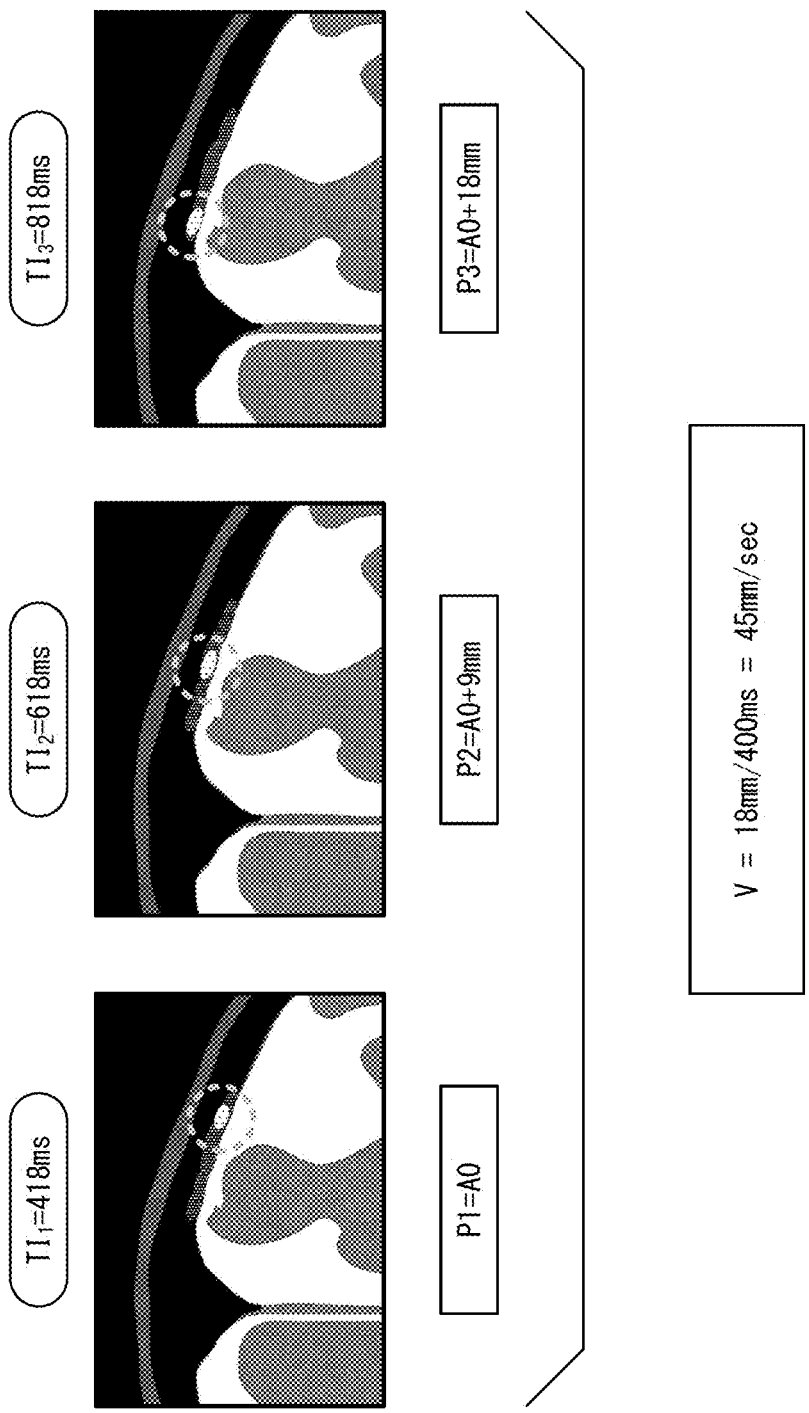
FIG. 15 is a diagram schematically illustrating calculation of the flow velocity of dural lymphatic fluid (or flow velocity of neurofluid in perivascular space of intradural blood vessels) from a perfusion image.

FIG. 15 is a diagram schematically illustrating calculation of the flow velocity of the dural lymphatic fluid from a plurality of perfusion images having different delay time TIs. FIG. 15 illustrates three parietal perfusion images that are acquired at different delay time TIs of 11=418 ms, 618 ms, and 818 ms. In each perfusion image, the high-brightness region surrounded by the broken-line circle corresponds to the dural lymphatic fluid labeled by the tag pulse. For example, on the basis of the image on the left side of FIG. 15 corresponding to the delay time 11=418 ms and the image on the right side of FIG. 15 corresponding to the delay time 11=818 ms, it is determined that the movement amount Δx of the high-brightness region corresponding to the increment ΔT (=400 ms) of the delay time TI is 18 mm. In this case, the moving speed of the high-brightness region, i.e., the flow velocity V of the dural lymphatic fluid can be estimated to be V=18 mm/400 ms=45 mm/sec.

(Specific Pulse Sequences)

Figure 16:
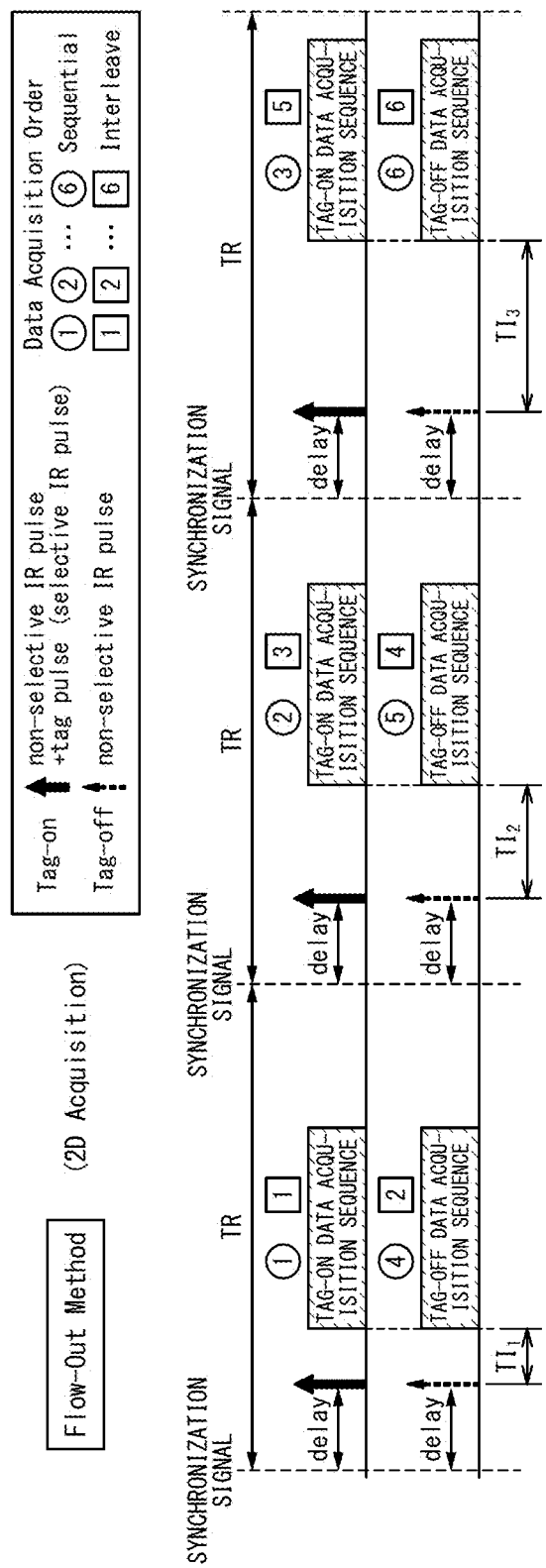
FIG. 16 is a diagram illustrating a pulse sequence for generating two-dimensional perfusion images or two-dimensional fused images under a Flow-out method.
Figure 17:
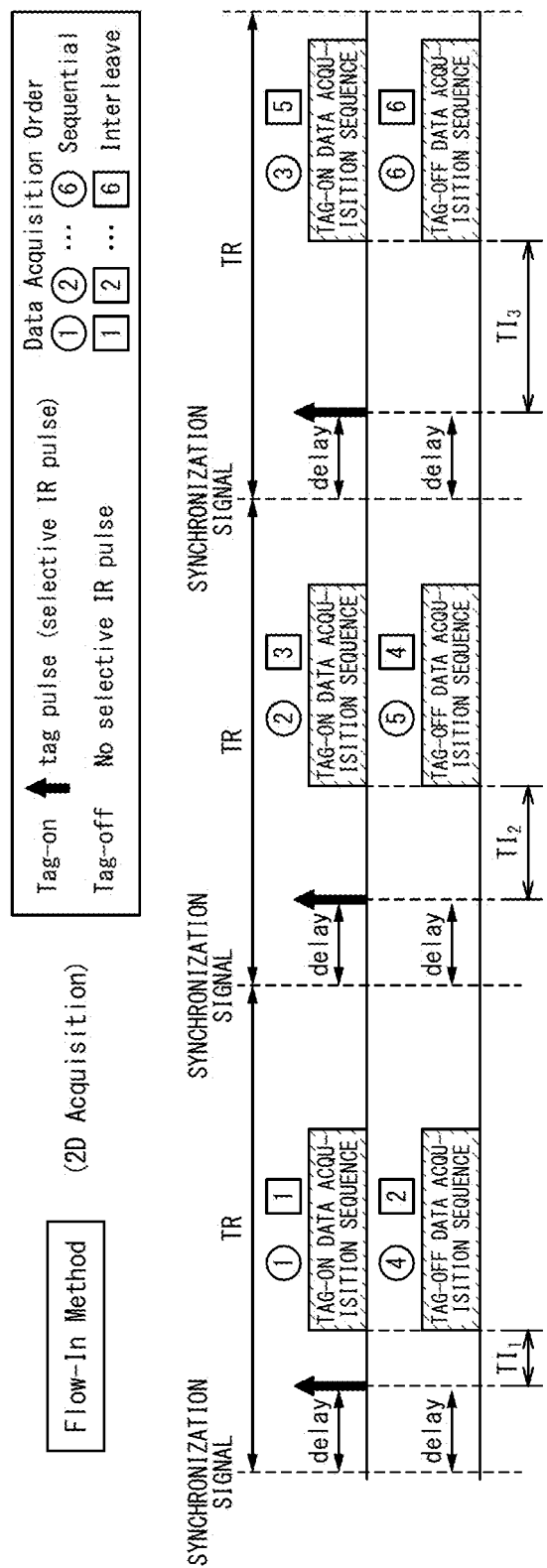
FIG. 17 is a diagram illustrating a pulse sequence for generating two-dimensional perfusion images or two-dimensional fused images under a Flow-in method.
Figure 18:
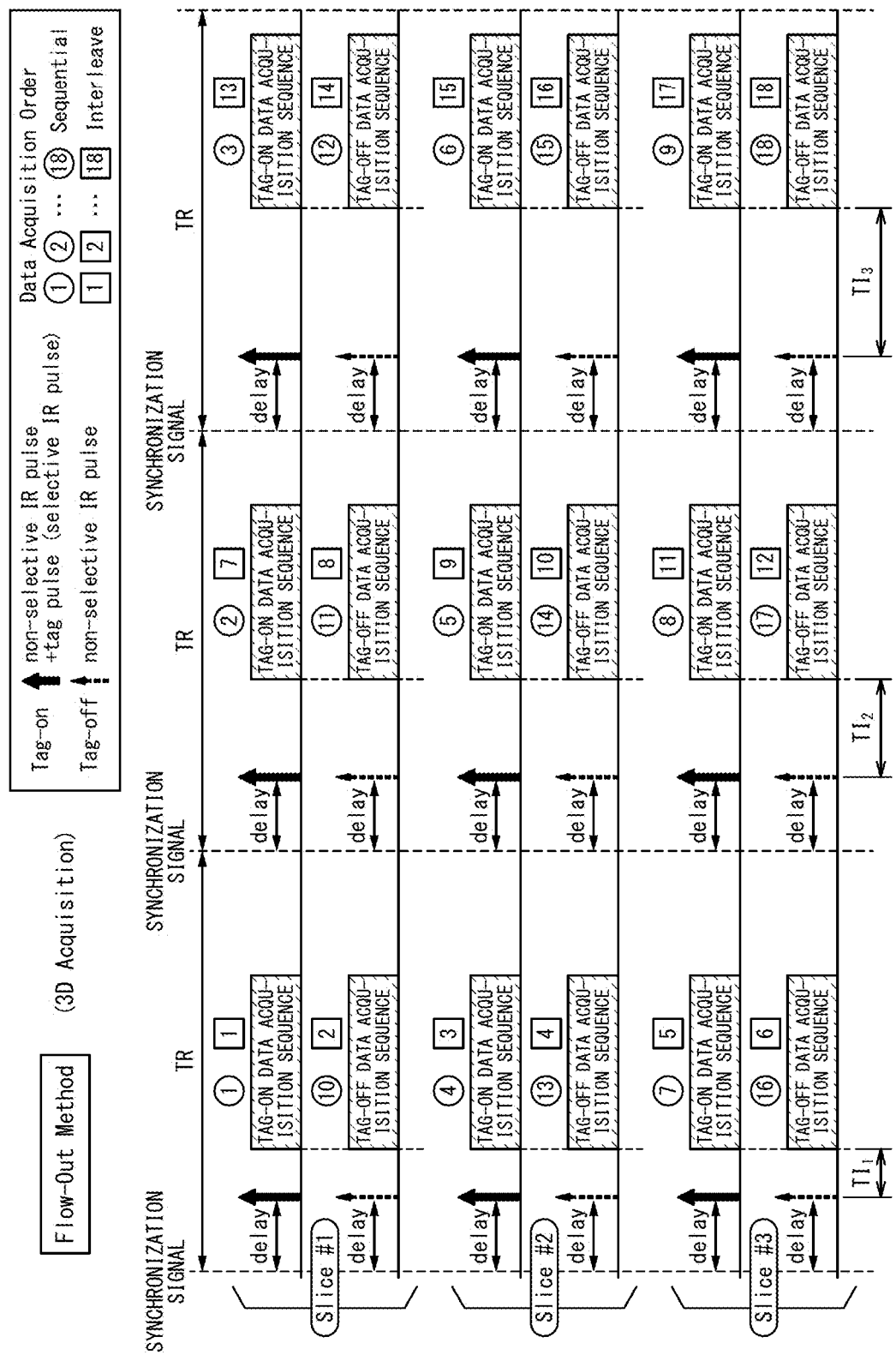
FIG. 18 is a diagram illustrating a pulse sequence for generating three-dimensional perfusion images or three-dimensional fused images under the Flow-out method.

In order to perform the above-described analysis, it is necessary to generate respective perfusion images or respective fused images corresponding to a plurality of different delay time TIs. FIG. 16 to FIG. 18 are diagrams illustrating pulse sequences, in each of which tag-on and tag-off data used for generating perfusion images and/or fused images are acquired at a plurality of different delay time TIs.

FIG. 16 illustrates a pulse sequence used for acquiring two-dimensional data of the above-described two-dimensional perfusion images or two-dimensional fused images under the Flow-out method. The synchronization signal shown in the sequence diagram of FIG. 16 is a gating signal for synchronization used for gating imaging (i.e., synchronization imaging). For example, in cardiac gating imaging such as ECG gating imaging and PPG gating imaging, an ECG (electrocardiographic gating) signal and/or a PPG (peripheral pulse gating) signal is used as a synchronization signal. Here, the cardiac gating imaging is synchronization imaging based on the circulatory system including the heart. Further, in the respiratory synchronization imaging called respiratory (RESP) gating, the respiratory signal detected by a respiratory sensor is used as the synchronization signal, for example.

FIG. 16 illustrates a sequence diagram used for acquiring tag-on data and tag-off data at a plurality of different delay time TIs. Although a sequence diagram corresponding to the delay times $TI_1$, $TI_2$, and $TI_3$ are illustrated in FIG. 16 from the viewpoint of simplification, the number of delay time is not limited particular number and any n delay time TIs from the delay time $TI_1$ to $TI_n$ can be set in general.

When acquiring tag-on data, a non-selective IR pulse is applied after elapse of a predetermined delay time from the synchronization signal, and then a tag pulse (i.e., selective IR pulse) is applied immediately after application of the non-selective IR pulse. In FIG. 16, the non-selective IR pulse and the tag pulse are collectively indicated by the thick solid-line arrow. After elapse of the delay time $Ti_n$ (n=1 to 3) from the non-selective IR pulse and the tag pulse, the tag-on data acquisition sequence is started.

On the other hand, when acquiring tag-off data, only the non-selective IR pulse is applied after elapse of the predetermined delay time from the synchronization signal. In FIG. 16, the non-selective IR pulse is indicated by the thin broken-line arrow. After elapse of the delay time $Ti_n$ (n=1 to 3) from the non-selective IR pulse, the tag-off data acquisition sequence is started.

As an order of acquiring tag-on data and tag-off data, a sequential acquisition order and an interleave acquisition order can be considered. According to the sequential acquisition order, all the tag-on data are first acquired for each delay time $TI_n$ (n=1 to 3), and then all the tag-off data are acquired for each delay time $TI_n$ (n=1 to 3). In FIG. 16, the order of the sequential acquisition is indicated by circled numbers.

Meanwhile, according to the interleave acquisition order, tag-on data and tag-off data are acquired alternately for each delay time. In FIG. 16, the order of interleave acquisition is indicated by each number surrounded by a square.

Note that the tag-on data and tag-off data can be acquired by ungated imaging without using a cardiac gating signal or a respiratory gating signal. In this case, the repetition time TR of data acquisition is set to a predetermined fixed time.

On the other hand, FIG. 17 illustrates a pulse sequence to be used for acquiring two-dimensional data of two-dimensional perfusion images or two-dimensional fused images under the Flow-in method. The differences in sequence diagram between the Flow-in method shown in FIG. 17 and the Flow-out method shown in FIG. 16 are the following two points.

Firstly, as to the acquisition of tag-on data, two IR pulses including the non-selective IR pulse and the tag pulse (i.e., selective IR pulse) are applied in the Flow-out method, whereas only the tag pulse (i.e., selective IR pulse only) is applied in the Flow-in method.

Secondly, as to the acquisition of tag-off data, one IR pulse, i.e., the non-selective IR pulse is applied in the Flow-out method, whereas no IR pulse is applied in the Flow-in method.

Except for above-described two points, the sequence diagram of the Flow-in method shown in FIG. 17 is the same as the sequence diagram of the Flow-out method shown in FIG. 16, and duplicate description is omitted.

FIG. 18 illustrates a pulse sequence used for acquiring three-dimensional data for each of different delay time TIs under the Flow-out method and generating three-dimensional perfusion images (or three-dimensional fused images) for the respective delay time TIs.

For three-dimensional perfusion images (or three-dimensional fused images), tag-on data and tag-off data are acquired from each of a plurality of slices. Although FIG. 18 illustrates a sequence diagram in which respective data only from three slices #1 to #3 are acquired from the viewpoint of simplification, the number of slices is not limited to three.

Also in the case of three-dimensional data acquisition, a sequential acquisition order and an interleave acquisition order can be considered. In the sequential acquisition order, tag-on data for the slice #1 are acquired at each delay time $TI_n$ (n=1 to 3), and the same sequence segment is repeated for each of the rest of the slices (i.e., slices #2 and #3 in this case). Next, tag-off data for the slice #1 are acquired at each delay time $TI_n$ (n=1 to 3), and the same sequence segment is repeated for each of the rest of the slices (i.e., slices #2 and #3 in this case). In this manner, tag-on data and tag-off data are acquired for every slice at all of the delay time TIs. In FIG. 18, the acquisition order of sequential acquisition is indicated by circled numbers, as well as in FIGS. 16 and 17.

In the interleave acquisition order, at the delay time III, the tag-on data and the tag-off data for the slice #1 are acquired, and the tag-on data and the tag-off data are subsequently acquired for each of the rest of the slices (i.e., slices #2 and #3 in this case). Next, after changing the delay time to $TI_2$, tag-on data and tag-off data are acquired for each of the slices #1, #2, and #3. Similarly, after changing the delay time to $TI_3$, tag-on data and tag-off data are acquired for each of the slices #1, #2, and #3. In this manner, tag-on data and tag-off data are acquired for every slice at all of the delay time TIs. Also in FIG. 18, the acquisition order of the interleave acquisition is indicated by each number surrounded by a square.

According to each of the pulse sequences described above, two-dimensional or three-dimensional tag-on data and tag-off data for a plurality of delay time TIs can be acquired in substantially one time imaging and in a short time.

With the use of the GUI (Graphical User Interface) via the input I/F 43 and the display 42, the user can appropriately set the delay time TI and select whether to adopt the sequential acquisition or interleave acquisition.

Each of FIG. 16 to FIG. 18 described above shows a pulse sequence in which the tag pulse is applied after elapse of a fixed predetermined delay time from the synchronization signal, and then a plurality of tag-on data are acquired, while the delay time TI from the tag pulse is being changed. Tag-off data are also acquired at the same timing as each of tag-on data.

On the other hand, in the pulse sequence shown in FIG. 19B, the time length from the synchronization signal to the start of acquiring the tag-on data is defined as the delay time and the tag-on data are acquired by keeping the delay time constant. Tag-off data are also acquired at the same timing as the tag-on data, although it is omitted in FIG. 19B.

For comparison with the pulse sequence shown in FIG. 19B, FIG. 19A shows the same pulse sequence segment of tag-on data acquisition shown in FIG. 16.

The synchronization signal is a cardiac gating signal such as an ECG signal or a PPG signal, or a respiratory gating signal. It should be noted that the pulse sequence shown in FIG. 19B has an advantage that the tag-on data and tag-off data are acquired in the same cardiac time phase or in the same respiratory time phase. The pulse sequence shown in FIG. 19B is hereinafter referred to as a constant time-phase pulse sequence.

The constant time-phase pulse sequence is the same as the pulse sequence shown in FIG. 16 to FIG. 18, in that a plurality of tag-on data (and tag-off data) are sequentially acquired while the delay time TI from the tag pulse is being changed. However, note that, in the constant time-phase pulse sequence, the time interval from the synchronization signal to the tag pulse changes depending on the delay time TI.

In the constant time-phase pulse sequence shown in FIG. 19B, every delay time TI is shorter than the interval between two adjacent synchronization signals.

Figure 20:
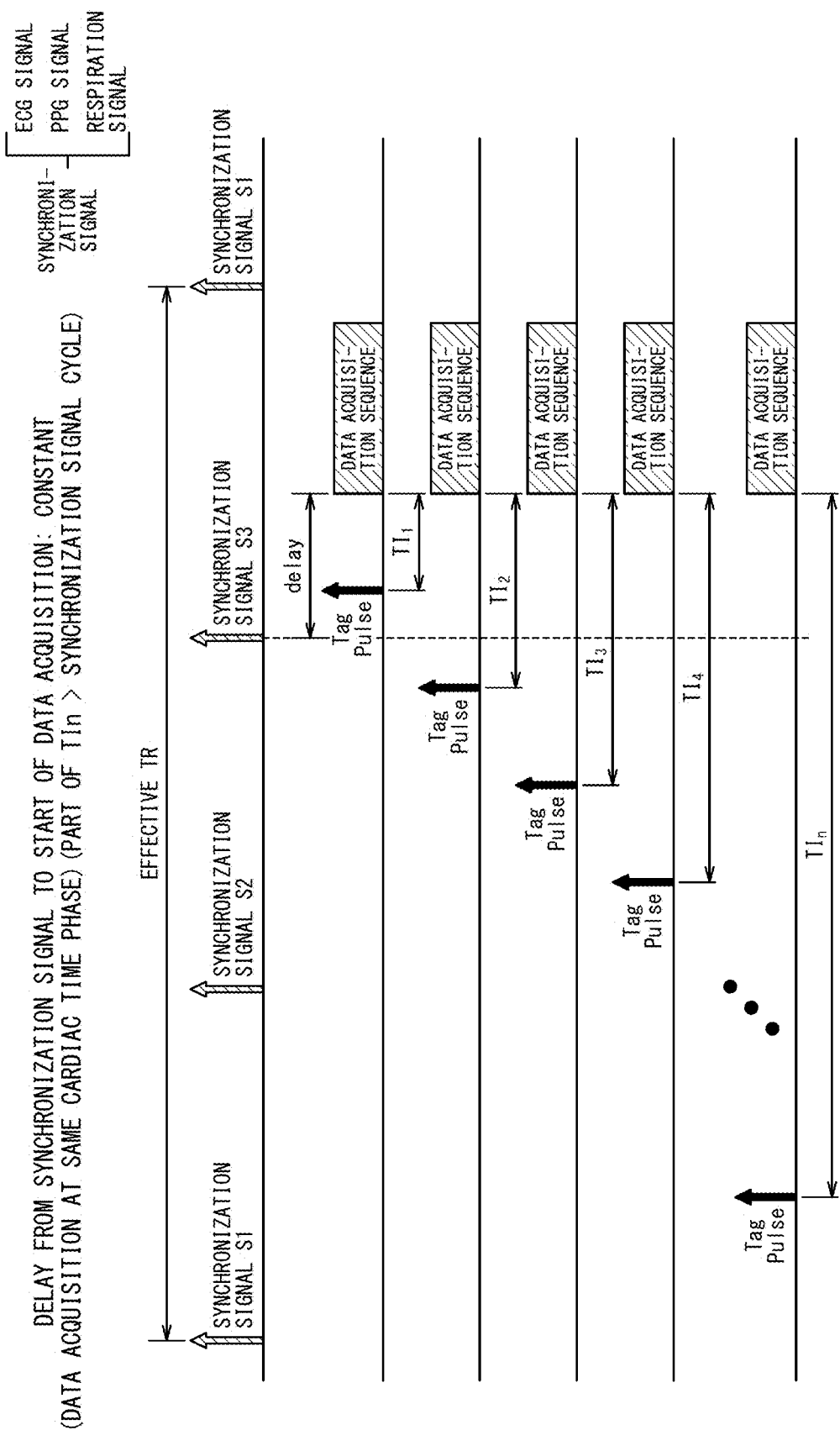
FIG. 20 is a diagram illustrating a constant time-phase pulse sequence in which some of delay time TIs are set to be longer than the interval between two adjacent synchronization signals.

In contrast to the pulse sequence shown in FIG. 19B, FIG. 20 illustrates a constant time-phase pulse sequence in the case where a part of delay time TIs are set longer than the interval between two adjacent synchronization signals. In the case of FIG. 20, all the tag-on data (and tag-off data) are acquired after elapse of a fixed delay time from the synchronization signal S3, whereas some tag-on pulses are applied between the synchronization signals S2 and S3, or between the synchronization signals S1 and S2, both of the synchronization signals S2 and S1 arriving before the synchronization signal S3. Due to such application timing of the tag-on pulse and acquisition timing of the tag-on data (and tag-off data), delay time TIs longer than a period of the synchronization signal can be set in this pulse sequence.

In the pulse sequence shown in FIG. 20, the period of the synchronization signals may change due to the fluctuation of the cardiac cycle, and consequently, it may happen that the increment ΔT of the delay time TI cannot always be set to be the same. However, the time interval from the tag pulse to the start of acquisition of the tag-on data (and tag-off data), i.e., the value of the actual delay time TI can be recognized by the apparatus for each delay time TI. Thus, as to generation of the perfusion curve, the perfusion curve can be plotted by using the actual delay time TI.

(Other Aspects of Perfusion Analysis)

As described above, the perfusion curve can be calculated from the relationship between the delay time TI and the pixel values of the perfusion image (or fused image) with respect to the delay time TI. The calculated perfusion curve enables calculation of parameters related to perfusion of body fluid such as the dural lymphatic fluid. For example, time to peak TTP, mean transition time MTT, relative dural lymphatic fluid volume rDLFV, and relative dural lymphatic fluid flow rDLFF can be calculated from the perfusion curve.

Further, the inventors of the present invention have shown that analysis using the pixel values of the perfusion images (or fused images) for the respective delay time TIs and the calculated perfusion curve provides insights with respect to what causes the perfusion of neurofluid such as the dural lymphatic fluid (i.e., findings with respect to what the driving force of the perfusion of neurofluid is).

Each of FIG. 21A to FIG. 21C is a graph obtained by calculating and plotting the perfusion curve of the dural lymphatic fluid perfusing inside the dura mater from the data acquired by any one of the pulse sequences shown in FIG. 16 to FIG. 18. More specifically, in each of FIG. 21A to FIG. 21C, the normalized pixel values of the dural lymphatic fluid at a specific pixel position in the dura mater are obtained for the respective different delay time TIs and are indicated as raw data by black square dots, and a perfusion curve calculated by curve-fitting these raw data with a curve defined by the gamma variate function shown in Expression 3 is indicated by a solid line.

FIG. 21A illustrates raw data and a perfusion curve that are calculated from data acquired by ungated imaging.

FIG. 21B illustrates raw data and a perfusion curve that are calculated from data acquired by cardiac gating imaging, especially PPG gating imaging with the use of PPG signals. It is considered that substantially the same graph as FIG. 21B may be also generated even when raw data and a perfusion curve are generated from data acquired by the ECG gating imaging instead of the PPG gating imaging.

FIG. 21C illustrates raw data and a perfusion curve that are calculated from data acquired by RESP (respiratory) gating imaging.

Of FIG. 21A to FIG. 21C, the deviation between the raw data and the perfusion curve is significantly large in FIG. 21A corresponding to ungated imaging and FIG. 21C corresponding to respiratory gating imaging, which indicates that the curve fitting by the gamma variate function is inappropriate. Contrastively, FIG. 21B corresponding to cardiac gating imaging shows that the deviation between the raw data and the perfusion curve is small and the curve fitting by the gamma variate function is performed most appropriately.

From this analysis result, it can be presumed that the perfusion of the dural lymphatic fluid (or perfusion of neurofluid in perivascular space around dural blood vessels) is driven by the driving force corresponding to the cardiac gating imaging. In other words, it can be presumed that the driving force for the perfusion of the dural lymphatic fluid is the blood pumped by the heartbeat.

From the matching degree between the raw data acquired by the gating method corresponding to a plurality of different driving forces (for example, the respiratory gating method and the cardiac gating method) and the fitting curve of the perfusion curve obtained from these raw data, the driving force for the perfusion of the target body fluid can be presumed. For example, contrary to the case of FIG. 21A to FIG. 21C, when the matching degree between the raw data of body fluid obtained by respiratory gating imaging and the fitting curve of the perfusion curve obtained from these raw data is higher than the case of the cardiac gating method, the driving force for the perfusion of the body fluid can be presumed to be respiratory motion.

As described above, the MRI apparatus of the above-described embodiments can observe the perfusion behavior of body fluid including cerebrospinal fluid and/or dural lymphatic fluid in real time without using a contrast agent.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An MRI apparatus, comprising:
    a scanner that includes a static magnetic field magnet configured to generate a static magnetic field, a gradient coil configured to generate a gradient magnetic field, and a WB (Whole Body) coil configured to apply an RF pulse to an object; and
    processing circuitry configured to
        cause the scanner to image, under a first imaging method, a tissue including a perfusion route of body fluid that removes waste products of the object under a first imaging method of depicting the body fluid hyperintensely, wherein the body fluid is neurofluid presumed to flow out through a wall of a superior sagittal sinus (SSS),
        generate an anatomical image of the tissue from first data acquired by imaging under the first imaging method, wherein the anatomical image is an image that depicts a region including a subarachnoid space (SAS), a superior sagittal sinus (SSS), a wall of the superior sagittal sinus, and a parasagittal dura (PSD),
        cause the scanner to image perfusion behavior of the body fluid in real time under a second imaging method using non-contrast perfusion imaging,
        generate a perfusion image indicating the perfusion behavior of the body fluid from second data acquired by imaging under the second imaging method, and
        generate a fused image by combining the anatomical image and the perfusion image.

2. The MRI apparatus according to claim 1, wherein:
    the second imaging method is an imaging method in which tag-on data are acquired from a predetermined imaging region after applying a tag pulse to at least one predetermined tag region and tag-off data are acquired from the predetermined imaging region without applying the tag pulse, the tag-on data being acquired after elapse of a predetermined delay time TI from application of the tag pulse; and
    the processing circuitry is further configured to generate the perfusion image by using a tag-on image generated from the tag-on data and a tag-off image generated from the tag-off data.

3. The MRI apparatus according to claim 2, wherein the processing circuitry is further configured to:
    set an efflux region of interest to a region where the body fluid is presumed to flow out;
    set the at least one predetermined tag region to a region through which the body fluid flows, which is close to the efflux region of interest, and which does not include the efflux region of interest; and
    generate the perfusion image as a Flow-Out image that depicts efflux of the body fluid flowing from the at least one predetermined tag region into the efflux region of interest.

4. The MRI apparatus according to claim 3, wherein the processing circuitry is further configured to set the efflux region of interest to a region that includes the superior sagittal sinus (SSS), the wall of the superior sagittal sinus, and the parasagittal dura (PSD), and does not include the subarachnoid space (SAS).

5. The MRI apparatus according to claim 3, wherein:
    the at least one predetermined tag region comprises a plurality of tag regions that are set by the processing circuitry; and
    the processing circuitry is further configured to generate the perfusion image as a flow-out image that depicts the body fluid flowing out of the plurality of tag regions into the efflux region of interest in a plurality of directions.

6. The MRI apparatus according to claim 2, wherein the processing circuitry is further configured to:
    set the efflux region of interest to a region where the body fluid is presumed to flow out;
    set the efflux region of interest as the at least one predetermined tag region; and
    generate the perfusion image as a Flow-In image that depicts influx of the body fluid flowing into the at least one predetermined tag region from an outside thereof.

7. The MRI apparatus according to claim 3, wherein the processing circuitry is further configured to:
    normalize, at each of same pixel positions between the tag-on image and the tag-off image, an absolute value of a difference in pixel value between the tag-on image and the tag-off image by dividing the absolute value of the difference by an absolute value of a pixel value of the tag-off image; and
    generate the perfusion image by using the normalized pixel values.

8. The MRI apparatus according to claim 6, wherein the processing circuitry is further configured to:
    normalize, at each of same pixel positions between the tag-on image and the tag-off image, an absolute value of difference in pixel value between the tag-on image and the tag-off image by dividing the absolute value of the difference by an absolute value of a pixel value of the tag-off image; and
    generate the perfusion image by using the normalized pixel values.

9. The MRI apparatus according to claim 1, wherein the processing circuitry is further configured to:
    set an efflux region of interest to a region where the body fluid is presumed to flow out;
    set a mask region that corresponds to the efflux region of interest; and
    generate a fused image by combining a modified anatomical image and a modified perfusion image, the modified anatomical image being obtained by eliminating the mask region from the anatomical image, the modified perfusion image being obtained by extracting only the mask region from the perfusion image.

10. The MRI apparatus according to claim 1, wherein the processing circuitry is further configured to:
  generate a plurality of perfusion images that correspond to a plurality of different delay times by using the second data acquired at the plurality of different delay times; and
  generate a plurality of fused images corresponding to the plurality of different delay times by combining the plurality of perfusion images and the anatomical image.

11. The MRI apparatus according to claim 10, wherein the processing circuitry is further configured to:
  normalize, at each of same pixel positions between a tag-on image and a tag-off image, an absolute value of difference in pixel value between the tag-on image and the tag-off image by dividing the absolute value of the difference by an absolute value of a pixel value of the tag-off image; and
  generate the plurality of perfusion images by using the normalized pixel values.

12. The MRI apparatus according to claim 11, wherein the processing circuitry is further configured to:
  set a region where the body fluid is presumed to flow out, as an efflux region of interest for each of the plurality of perfusion images;
  extract a specific pixel value in the efflux region of interest from each of the plurality of perfusion images; and
  calculate a perfusion curve from a plurality of extracted specific pixel values and a plurality of delay times corresponding to the plurality of extracted specific pixel values.

13. The MRI apparatus according to claim 12, wherein the processing circuitry is further configured to calculate the perfusion curve by curve-fitting the plurality of extracted specific pixel values and the plurality of delay times corresponding to the plurality of extracted specific pixel values to a predetermined curve.

14. The MRI apparatus according to claim 13, wherein the predetermined curve is a curve defined by a gamma variate function represented by $$y = p1 \cdot (TI)^{p2} \cdot \exp[-(TI)/p3] + p4,$$

wherein, TI is the delay time, and p1, p2, p3, and p4 are constants.

15. The MRI apparatus according to claim 13, wherein the processing circuitry is further configured to calculate the perfusion curve by curve-fitting, by using at least four different delay times and at least four pixel values corresponding to the at least four different delay times.

16. The MRI apparatus according to claim 15, wherein, (i) the body fluid that removes waste products of the object is dural lymphatic fluid presumed to flow out through the wall of the superior sagittal sinus (SSS), and (ii) a peak position of a perfusion curve of the dural lymphatic fluid is presumed to be at a delay time of approximately 1.2 seconds, and wherein
  the plurality of delay times are set as respective positions of a total of six points that includes:
  one point between 0.4 seconds and 0.6 seconds in an presumed rising region of the perfusion curve;
  one point between 0.8 seconds and 1.16 seconds;
  one point between 1.2 seconds and 1.5 seconds near the peak position;
  one point between 1.5 seconds and 2.0 seconds; and
  two points after 2.5 seconds in a period presumed to be after a falling region of the perfusion curve.

17. The MRI apparatus according to claim 12, wherein:
  the body fluid that removes waste products of the object is dural lymphatic fluid presumed to flow out through a wall of a superior sagittal sinus (SSS); and
  the processing circuitry is further configured to calculate, form the perfusion curve, an index related to perfusion, the index including at least one of peak height PH, mean transition time MTT, time to peak TTP, rDLFV (relative dural lymphatic fluid volume), and rDLFF (relative dural lymphatic fluid flow).

18. The MRI apparatus according to claim 12, wherein the processing circuitry is further configured to be able to calculate the perfusion curve from any one of the perfusion image generated as a two-dimensional image and the perfusion image generated as a three-dimensional image.

19. The MRI apparatus according to claim 10, wherein the processing circuitry is further configured to:
  generate a plurality of difference images respectively corresponding to the plurality of different delay times by subtracting the plurality of perfusion images; and
  calculate a virtual flow velocity of the body fluid from a change in spread of a region of the body fluid depicted in the plurality of difference images.

20. An MRI apparatus, comprising:
  a scanner that includes a static magnetic field magnet configured to generate a static magnetic field, a gradient coil configured to generate a gradient magnetic field, and a WB (Whole Body) coil configured to apply an RF pulse to an object; and
  processing circuitry configured to
    cause the scanner to image, under a first imaging method, a tissue including a perfusion route of body fluid that removes waste products of the object, the body fluid including neurofluid,
    generate an anatomical image of the tissue from first data acquired by imaging under the first imaging method,
    cause the scanner to image perfusion behavior of the body fluid in real time under a second imaging method using non-contrast perfusion imaging,
    generate a perfusion image indicating the perfusion behavior of the body fluid from second data acquired by imaging under the second imaging method, and
    generate a fused image by combining the anatomical image and the perfusion image,
  wherein the processing circuitry is further configured to
    generate a plurality of perfusion images that correspond to a plurality of different delay times by using the second data acquired at the plurality of different delay times; and
    generate a plurality of fused images corresponding to the plurality of different delay times by combining the plurality of perfusion images and the anatomical image.

* * * * *